United States Patent
Schindler et al.

(10) Patent No.: US 8,178,022 B2
(45) Date of Patent: May 15, 2012

(54) METHOD OF MANUFACTURING AN ARTICLE OF FOOTWEAR WITH A FLUID-FILLED CHAMBER

(75) Inventors: Eric S. Schindler, Portland, OR (US); Stuart C. Forstrom, Beaverton, OR (US); Daniel W. Peter, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 238 days.

(21) Appl. No.: 11/957,821

(22) Filed: Dec. 17, 2007

(65) Prior Publication Data

US 2009/0151093 A1 Jun. 18, 2009

(51) Int. Cl.
*A43D 8/00* (2006.01)
*A43B 13/00* (2006.01)

(52) U.S. Cl. ...................... 264/261; 12/146 R; 12/146 B

(58) Field of Classification Search .................. 264/261; 36/29

See application file for complete search history.

(56) References Cited

U.S. PATENT DOCUMENTS

| | | |
|---|---|---|
| 2,677,906 A | 5/1954 | Reed |
| 2,703,770 A | 3/1955 | Melzer |
| 3,030,640 A | 4/1962 | Gosman |
| 3,608,215 A | 9/1971 | Fukuoka |
| 3,685,176 A | 8/1972 | Rudy |
| 3,758,964 A | 9/1973 | Nishimura |
| 4,187,620 A | 2/1980 | Selner |
| 4,217,705 A | 8/1980 | Donzis |
| 4,358,902 A | 11/1982 | Cole et al. |
| 4,506,460 A | 3/1985 | Rudy |
| 4,547,919 A | 10/1985 | Wang |
| 4,670,995 A | 6/1987 | Huang |
| 4,698,864 A | 10/1987 | Graebe |
| 4,722,131 A | 2/1988 | Huang |
| 4,782,602 A | 11/1988 | Lakic |
| 4,803,029 A | 2/1989 | Iversen et al. |
| 4,817,304 A | 4/1989 | Parker et al. |
| 4,823,482 A | 4/1989 | Lakic |
| 4,845,861 A | 7/1989 | Moumdjian |
| 4,874,640 A | 10/1989 | Donzis |
| 4,891,855 A | 1/1990 | Cheng-Chung |

(Continued)

FOREIGN PATENT DOCUMENTS

FR 1 011 213 A 6/1952

(Continued)

OTHER PUBLICATIONS

Invitation to Pay Additional Fees and Communication Relating to the Results of the Partial International Search in PCT Application No. PCT/US2008/079088, mailed Feb. 23, 2009.

(Continued)

*Primary Examiner* — Philip Tucker
*Assistant Examiner* — Vicki Wu
(74) *Attorney, Agent, or Firm* — Plumsea Law Group, LLC

(57) ABSTRACT

An article of footwear may have a sole structure with a chamber, a plate, and an outsole. The chamber encloses a fluid and has an upper surface and an opposite lower surface. The plate is positioned adjacent to the upper surface and has a plurality of projections that extend into indentations in the chamber. The outsole may be positioned adjacent to the lower surface and may have a plurality of projections that extend into indentations in the chamber. In some manufacturing processes for the sole structure, the plate and outsole may be located within a mold, and the chamber may then be shaped by surfaces of the plate, outsole, and mold.

20 Claims, 43 Drawing Sheets

U.S. PATENT DOCUMENTS

| | | | |
|---|---|---|---|
| 4,906,502 A | 3/1990 | Rudy | |
| 4,912,861 A | 4/1990 | Huang | |
| 4,991,317 A | 2/1991 | Lakic | |
| 4,999,931 A | 3/1991 | Vermeulen | |
| 5,022,109 A | 6/1991 | Pekar | |
| 5,025,575 A | 6/1991 | Lakic | |
| 5,042,176 A | 8/1991 | Rudy | |
| 5,044,030 A | 9/1991 | Balaton | |
| 5,158,767 A | 10/1992 | Cohen et al. | |
| 5,179,792 A | 1/1993 | Brantingham | |
| 5,193,246 A | 3/1993 | Huang | |
| 5,199,191 A | 4/1993 | Moumdjian | |
| 5,224,277 A | 7/1993 | Sang Do | |
| 5,224,278 A | 7/1993 | Jeon | |
| 5,228,156 A | 7/1993 | Wang | |
| 5,235,715 A | 8/1993 | Donzis | |
| 5,245,766 A | 9/1993 | Warren | |
| 5,253,435 A | 10/1993 | Auger et al. | |
| 5,257,470 A | 11/1993 | Auger et al. | |
| 5,258,421 A | 11/1993 | Lorenz et al. | |
| 5,335,382 A | 8/1994 | Huang | |
| 5,337,492 A | 8/1994 | Anderie et al. | |
| 5,353,459 A | 10/1994 | Potter et al. | |
| 5,363,570 A | 11/1994 | Allen | |
| 5,367,791 A | 11/1994 | Gross et al. | |
| 5,406,719 A | 4/1995 | Potter | |
| 5,493,792 A | 2/1996 | Bates et al. | |
| 5,572,804 A | 11/1996 | Skaja et al. | |
| 5,592,706 A | 1/1997 | Pearce | |
| 5,595,004 A | 1/1997 | Lyden et al. | |
| 5,669,161 A | 9/1997 | Huang | |
| 5,686,167 A | 11/1997 | Rudy | |
| 5,704,137 A | 1/1998 | Dean et al. | |
| 5,741,568 A | 4/1998 | Rudy | |
| 5,771,606 A | 6/1998 | Litchfield et al. | |
| 5,832,630 A | 11/1998 | Potter | |
| 5,846,063 A | 12/1998 | Lakic | |
| 5,907,911 A | 6/1999 | Huang | |
| 5,916,664 A | 6/1999 | Rudy | |
| 5,925,306 A | 7/1999 | Huang | |
| 5,952,065 A | 9/1999 | Mitchell et al. | |
| 5,976,451 A | 11/1999 | Skaja et al. | |
| 5,979,078 A | 11/1999 | McLaughlin | |
| 5,993,585 A | 11/1999 | Goodwin et al. | |
| 6,009,637 A | 1/2000 | Pavone | |
| 6,013,340 A | 1/2000 | Bonk et al. | |
| 6,027,683 A | 2/2000 | Huang | |
| 6,029,962 A | 2/2000 | Shorten et al. | |
| 6,065,150 A | 5/2000 | Huang | |
| 6,098,313 A | 8/2000 | Skaja | |
| 6,127,010 A | 10/2000 | Rudy | |
| 6,128,837 A | 10/2000 | Huang | |
| 6,192,606 B1 | 2/2001 | Pavone | |
| 6,253,466 B1 | 7/2001 | Harmon-Weiss et al. | |
| 6,374,514 B1 | 4/2002 | Swigart | |
| 6,385,864 B1 | 5/2002 | Sell, Jr. et al. | |
| 6,402,879 B1 | 6/2002 | Tawney et al. | |
| 6,430,843 B1 | 8/2002 | Potter et al. | |
| 6,457,262 B1 | 10/2002 | Swigart | |
| 6,463,612 B1 | 10/2002 | Potter | |
| 6,550,085 B2 | 4/2003 | Roux | |
| 6,571,490 B2 | 6/2003 | Tawney et al. | |
| 6,665,958 B2 | 12/2003 | Goodwin | |
| 6,783,184 B2 | 8/2004 | DiBattista et al. | |
| 6,796,056 B2 | 9/2004 | Swigart | |
| 6,837,951 B2 | 1/2005 | Rapaport | |
| 6,892,477 B2 | 5/2005 | Potter et al. | |
| 6,918,198 B2 | 7/2005 | Chi | |
| 6,931,764 B2 | 8/2005 | Swigart et al. | |
| 6,971,193 B1 | 12/2005 | Potter et al. | |
| 7,000,335 B2 | 2/2006 | Swigart et al. | |
| 7,051,456 B2 | 5/2006 | Swigart et al. | |
| 7,070,845 B2 | 7/2006 | Thomas et al. | |
| 7,076,891 B2 | 7/2006 | Goodwin | |
| 7,086,179 B2 | 8/2006 | Dojan et al. | |
| 7,086,180 B2 * | 8/2006 | Dojan et al. | 36/29 |
| 7,128,796 B2 | 10/2006 | Hensley et al. | |
| 7,131,218 B2 | 11/2006 | Schindler | |
| 7,141,131 B2 | 11/2006 | Foxen et al. | |
| 7,200,957 B2 | 4/2007 | Hubbard et al. | |
| 7,244,483 B2 | 7/2007 | Tawney et al. | |
| 7,707,745 B2 | 5/2010 | Schindler et al. | |
| 2004/0031170 A1 * | 2/2004 | Chi | 36/29 |
| 2004/0250448 A1 * | 12/2004 | Reed et al. | 36/29 |
| 2007/0006488 A1 | 1/2007 | Litchfield | |
| 2007/0074423 A1 * | 4/2007 | Goodwin et al. | 36/29 |
| 2007/0119075 A1 * | 5/2007 | Schindler et al. | 36/29 |

FOREIGN PATENT DOCUMENTS

| | | |
|---|---|---|
| FR | 1011213 A | 6/1952 |
| WO | WO 00/70981 A | 11/2000 |
| WO | WO 00/70981 A1 | 11/2000 |

OTHER PUBLICATIONS

International Search Report and Written Opinion in PCT Application No. PCT/US2008/079095, mailed Feb. 17, 2009.
International Search Report and Written Opinion in PCT Application No. PCT/US2008/079088, mailed Jun. 4, 2009.
PCT International Preliminary Search Report mailed on Jul. 1, 2010 for PCT/US2008/079088.
PCT International Preliminary Search Report mailed on Jul. 1, 2010 for PCT/US2008/079095.
Office Action mailed Feb. 3, 2011, for U.S. Appl. No. 11/957,761.

* cited by examiner

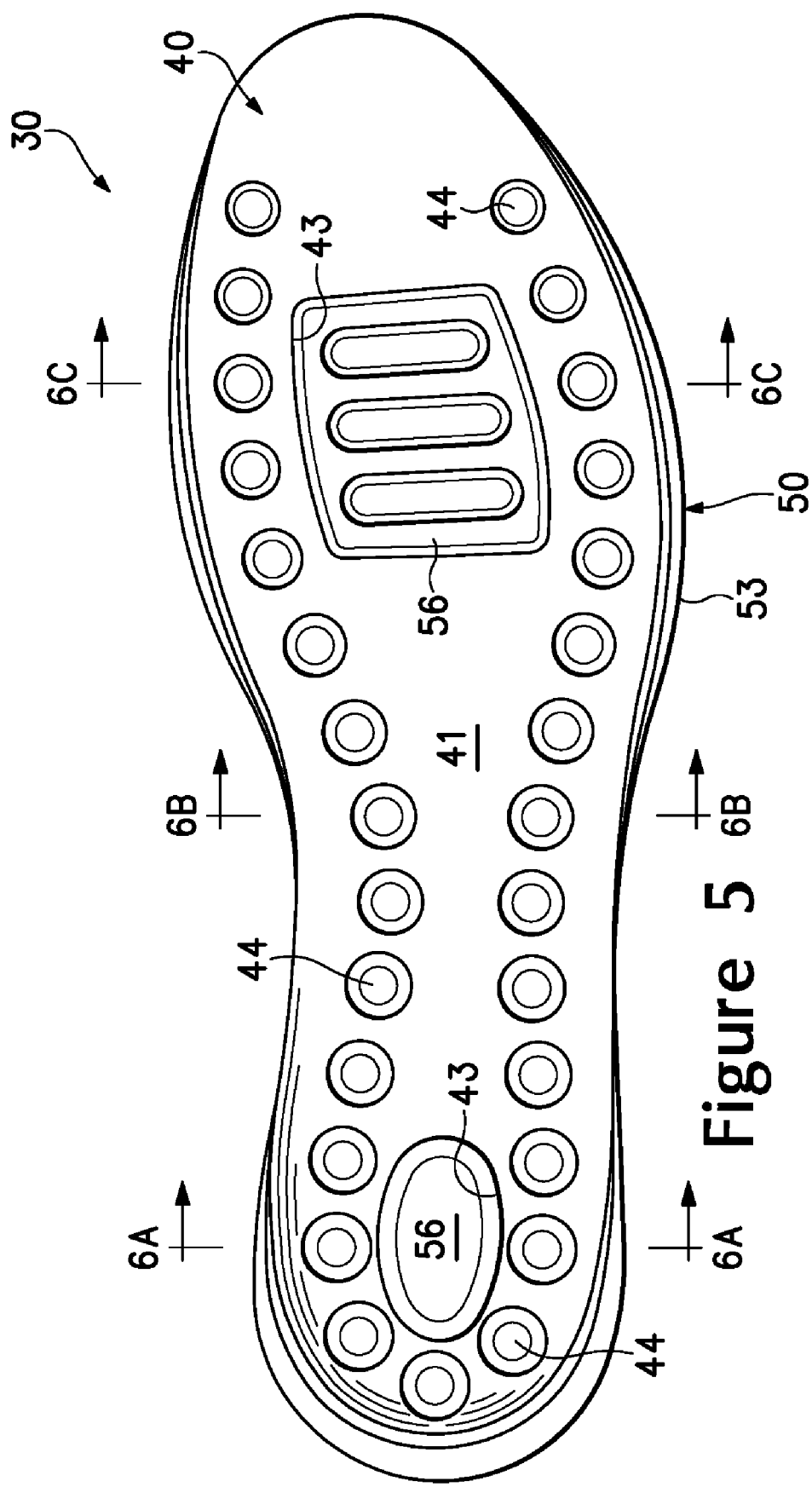

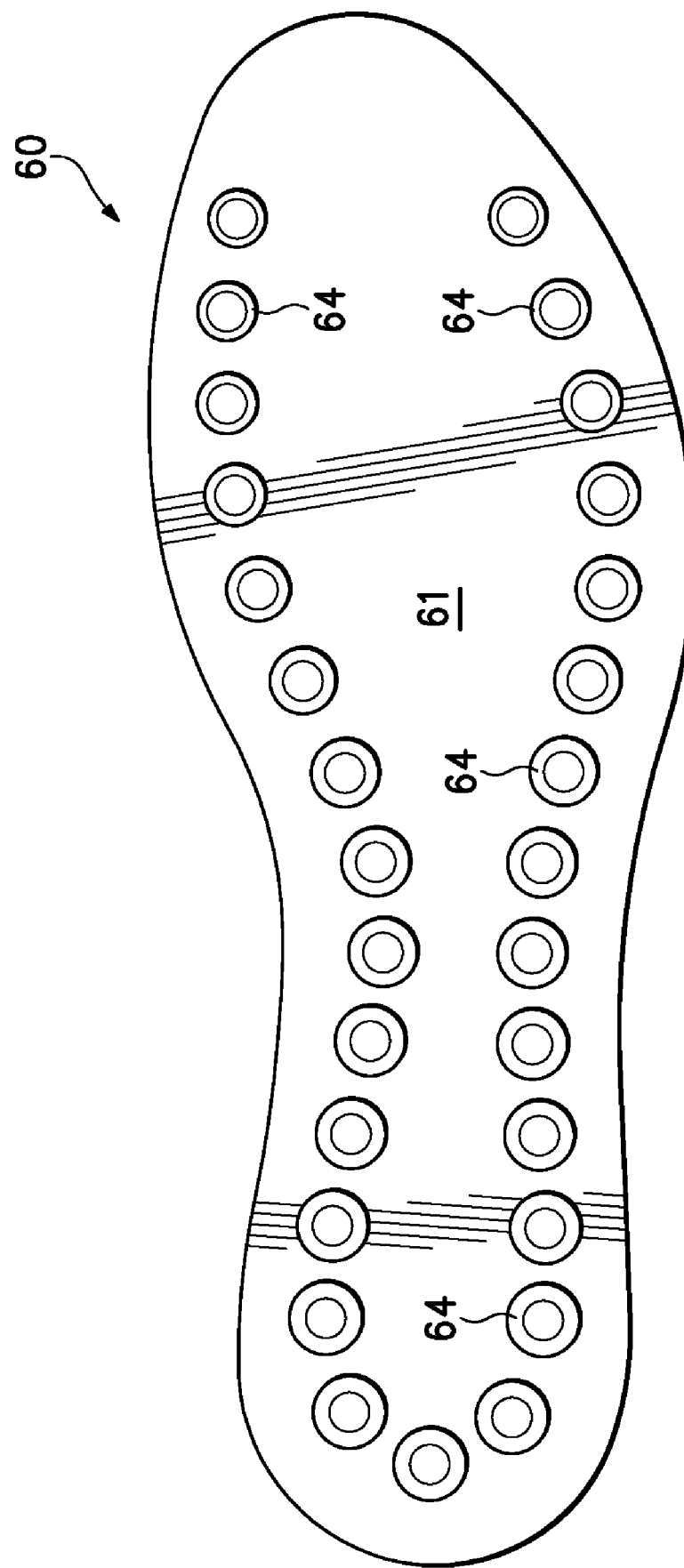

METHOD OF MANUFACTURING AN ARTICLE OF FOOTWEAR WITH A FLUID-FILLED CHAMBER

BACKGROUND

A conventional article of athletic footwear includes two primary elements, an upper and a sole structure. The upper may be formed from a plurality of material elements (e.g., textiles, leather, and foam materials) that define a void to securely receive and position a foot with respect to the sole structure. The sole structure is secured to a lower surface of the upper and is generally positioned to extend between the foot and the ground. In addition to attenuating ground reaction forces, the sole structure may provide traction, impart stability, and limit various foot motions, such as pronation. Accordingly, the upper and the sole structure operate cooperatively to provide a comfortable structure that is suited for a wide variety of ambulatory activities, such as walking and running.

The sole structure of an article of athletic footwear generally exhibits a layered configuration that includes a comfort-enhancing insole, a resilient midsole at least partially formed from a polymer foam material, and a ground-contacting outsole that provides both abrasion-resistance and traction. Suitable polymer foam materials for the midsole include ethylvinylacetate or polyurethane that compresses resiliently under an applied load to attenuate ground reaction forces. Conventional polymer foam materials compress resiliently, in part, due to the inclusion of a plurality of open or closed cells that define an inner volume substantially displaced by gas. Following repeated compressions, the cells of the polymer foam may deteriorate, thereby resulting in decreased compressibility and decreased force attenuation characteristics of the sole structure.

One manner of reducing the mass of a polymer foam midsole and decreasing the effects of deterioration following repeated compressions is to incorporate a fluid-filled chamber into the midsole. In general, the fluid-filled chambers are formed from a sealed elastomeric polymer material that may be pressurized. The chambers are then encapsulated in the polymer foam of the midsole such that the combination of the chamber and the encapsulating polymer foam functions as the midsole. In some configurations, textile or foam tensile members may be located within the chamber or reinforcing structures may be bonded to an exterior surface of the chamber to impart shape to or retain an intended shape of the chamber.

Fluid-filled chambers suitable for footwear applications may be manufactured by a two-film technique, in which two separate sheets of elastomeric film are formed to exhibit the overall peripheral shape of the chamber. The sheets are then bonded together along their respective peripheries to form a sealed structure, and the sheets are also bonded together at predetermined interior areas to give the chamber a desired configuration. That is, interior bonds (i.e., bonds spaced inward from the periphery) provide the chamber with a predetermined shape and size upon pressurization. In order to pressurize the chamber, a nozzle or needle connected to a fluid pressure source is inserted into a fill inlet formed in the chamber. Following pressurization of the chamber, the fill inlet is sealed and the nozzle is removed. A similar procedure, referred to as thermoforming, may also be utilized, in which a heated mold forms or otherwise shapes the sheets of elastomeric film during the manufacturing process.

Chambers may also be manufactured by a blow-molding technique, wherein a molten or otherwise softened elastomeric material in the shape of a tube is placed in a mold having the desired overall shape and configuration of the chamber. The mold has an opening at one location through which pressurized air is provided. The pressurized air induces the liquefied elastomeric material to conform to the shape of the inner surfaces of the mold. The elastomeric material then cools, thereby forming a chamber with the desired shape and configuration. As with the two-film technique, a nozzle or needle connected to a fluid pressure source is inserted into a fill inlet formed in the chamber in order to pressurize the chamber. Following pressurization of the chamber, the fill inlet is sealed and the nozzle is removed.

SUMMARY

An article of footwear may have an upper and a sole structure secured to the upper. The sole structure may include a chamber, an upper sole element, and a lower sole element. The chamber encloses a fluid and has an upper surface and an opposite lower surface. The upper surface defines a plurality of upper indentations extending downward and into the chamber, and the lower surface defines a plurality of lower indentations extending upward and into the chamber. The upper sole element is positioned adjacent to the upper surface and has a plurality of projections that extend into the upper indentations. Similarly, the lower sole element is positioned adjacent to the lower surface and has a plurality of projections that extend into the lower indentations.

A method of manufacturing a sole structure for an article of footwear may include inserting a first sole element and a second sole element into a mold. A polymer material is located between the first sole element and the second sole element. The polymer material is then shaped against surfaces of the first sole element, the second sole element, and the mold to form a fluid-filled chamber. The first sole element may be a plate and the second sole element may be an outsole. In some configurations, each of the plate and the outsole may have projections, and the chamber is formed such that the polymer material extends around the projections. The mold may also be utilized to seal fluid at either an ambient pressure or an elevated pressure within the chamber. Additionally, the polymer material may be a parison or sheets of the polymer material, for example.

The advantages and features of novelty characterizing aspects of the invention are pointed out with particularity in the appended claims. To gain an improved understanding of the advantages and features of novelty, however, reference may be made to the following descriptive matter and accompanying drawings that describe and illustrate various embodiments and concepts related to the invention.

FIGURE DESCRIPTIONS

The foregoing Summary and the following Detailed Description will be better understood when read in conjunction with the accompanying drawings.

FIG. 5 is a top plan view of the first sole structure.

FIG. 13 is a top plan view of an outsole of the first sole structure.

DETAILED DESCRIPTION

The following discussion and accompanying figures disclose various configurations of footwear sole structures that include chambers and other elements. The sole structures are disclosed with reference to footwear having a configuration that is suitable for running. Concepts associated with the sole structures are not limited to footwear designed for running, however, and may be utilized with a wide range of athletic footwear styles, including basketball shoes, tennis shoes, football shoes, cross-training shoes, walking shoes, and soccer shoes, for example. The concepts associated with the sole structures may also be utilized with footwear styles that are generally considered to be non-athletic, including dress shoes, loafers, sandals, and boots. Accordingly, the concepts disclosed herein apply to a wide variety of footwear styles.

General Footwear Structure

Figure 1:
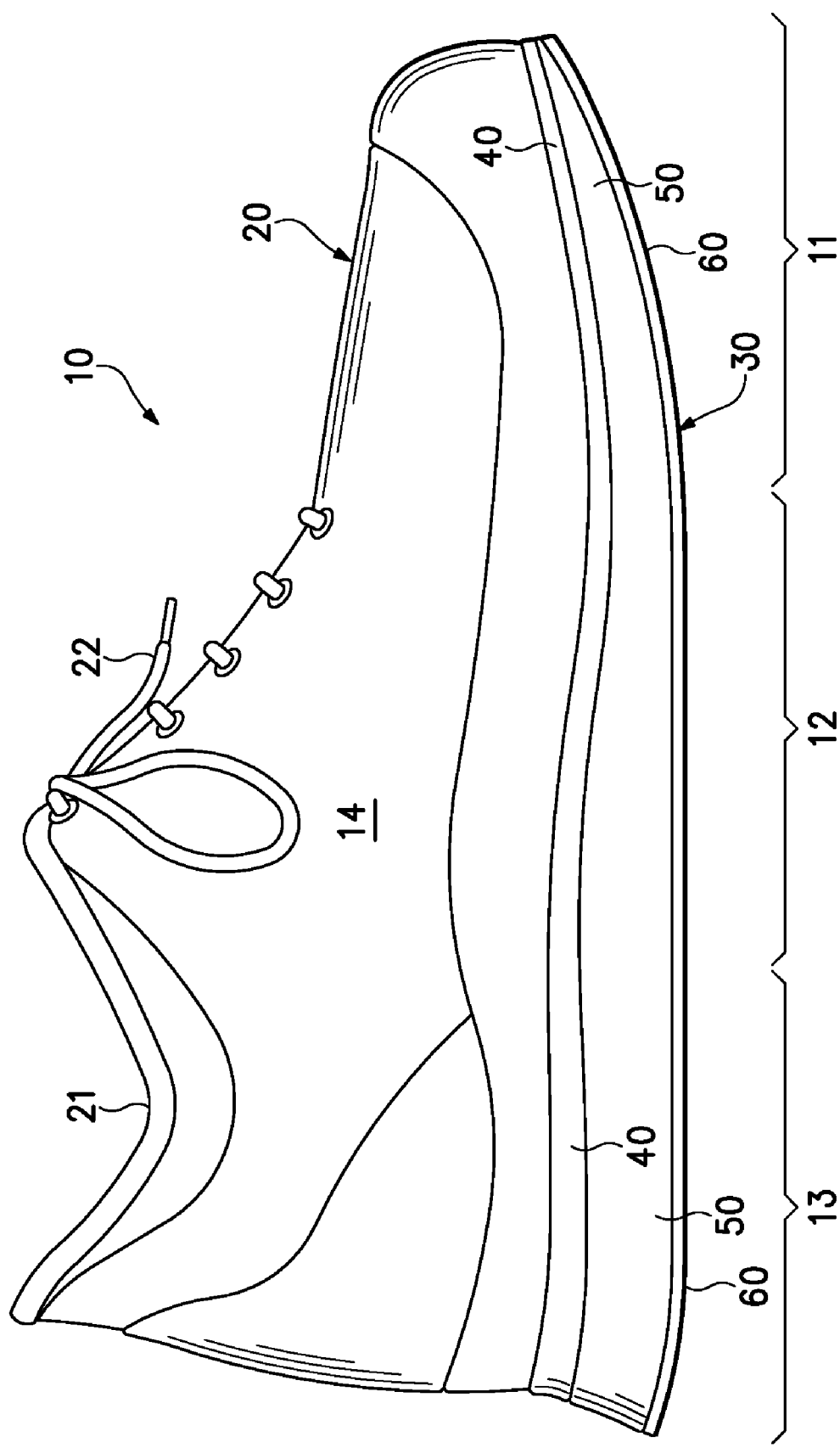
FIG. 1 is a lateral side elevational view of an article of footwear.
Figure 2:
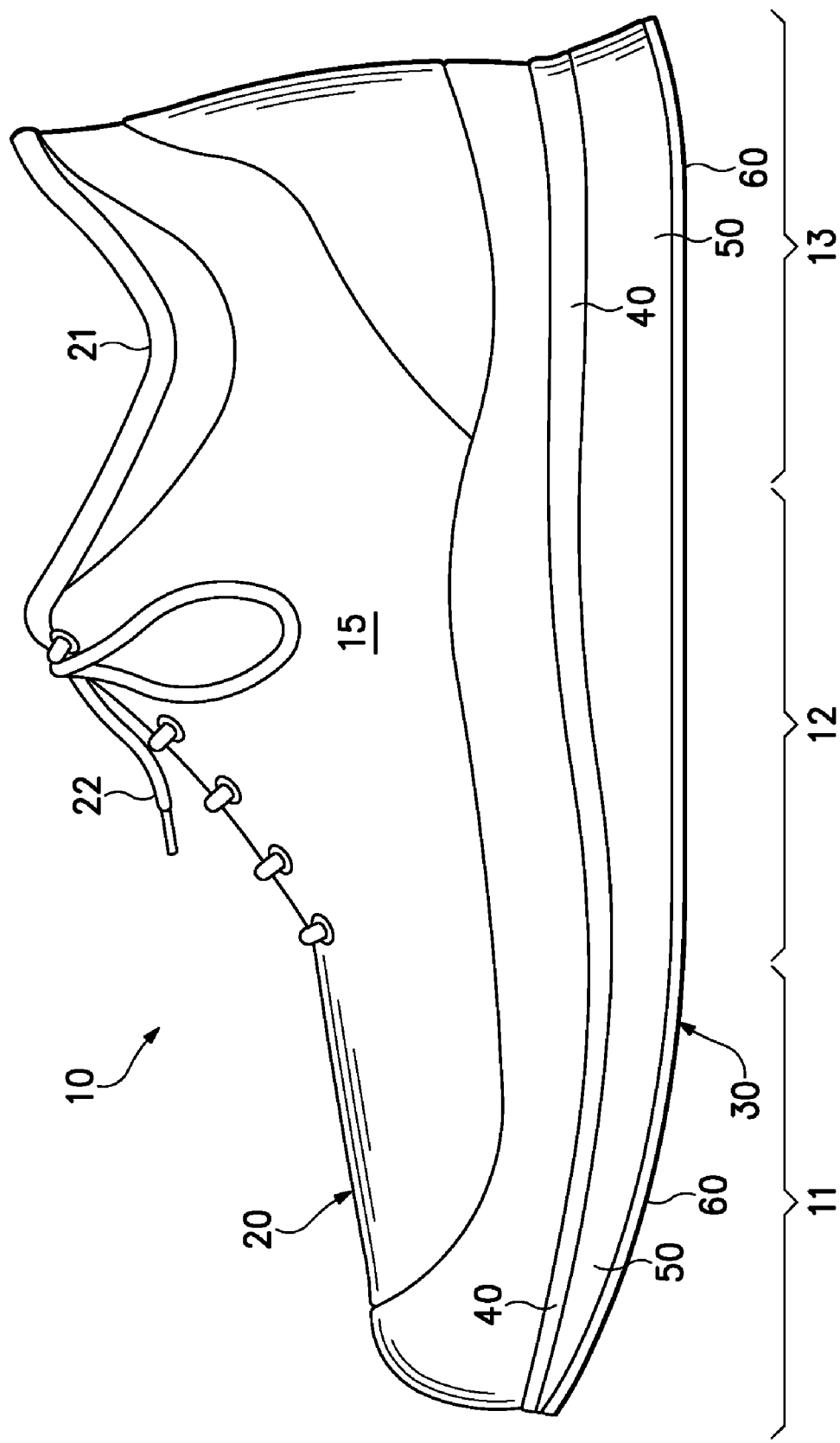
FIG. 2 is a medial side elevational view of the article of footwear.
Figure 3:
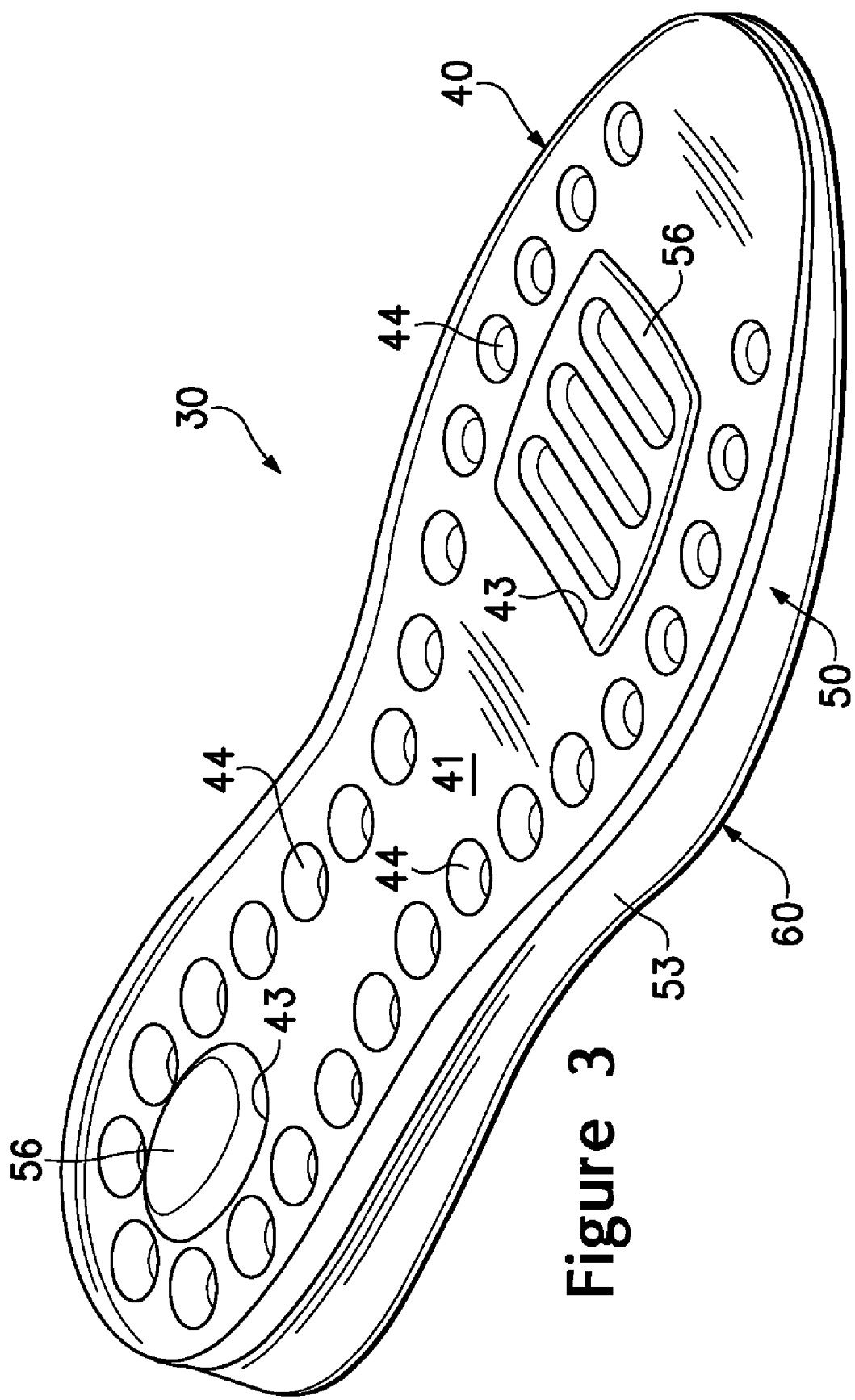
FIG. 3 is a perspective view of a first sole structure of the article of footwear.
Figure 4:
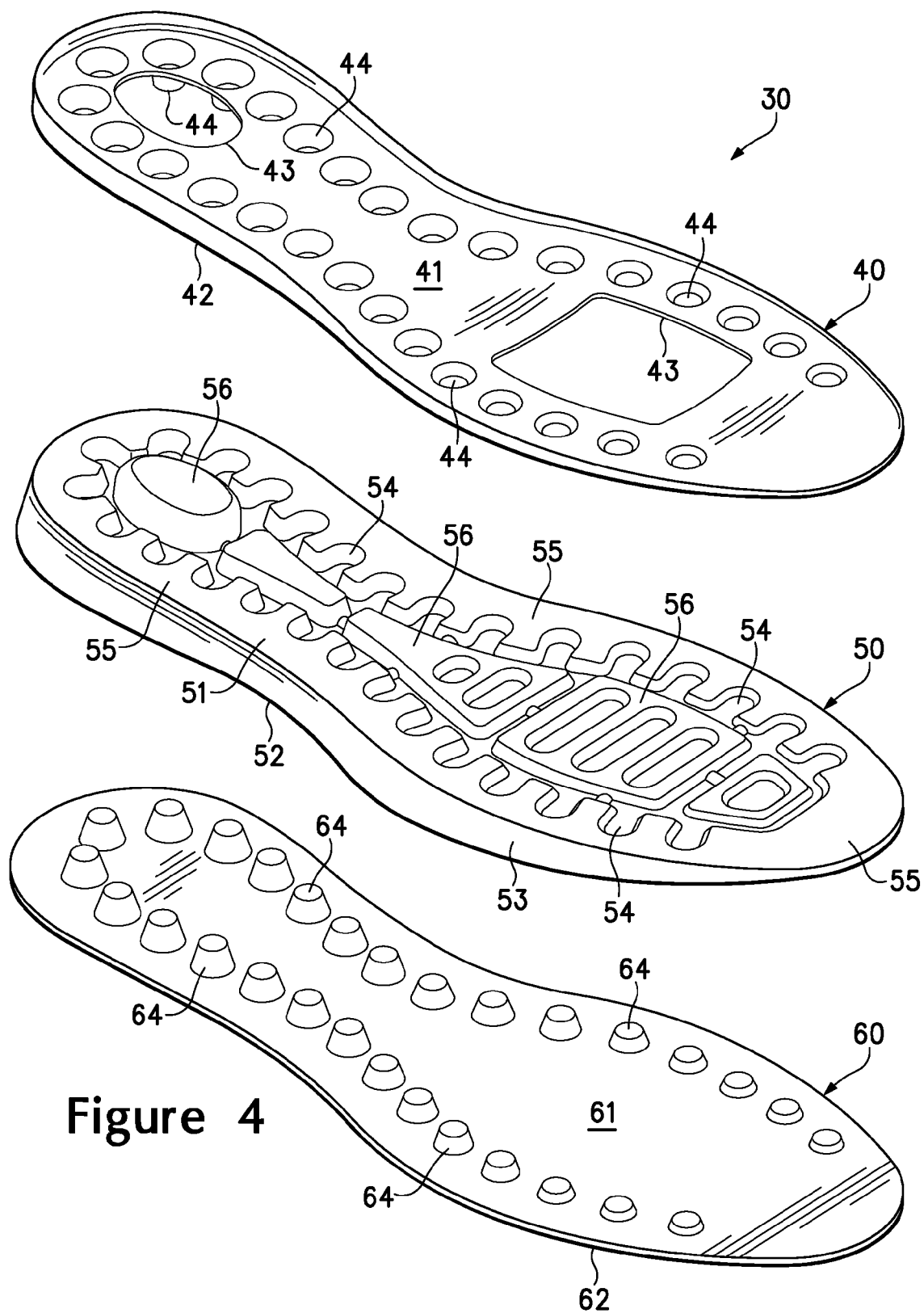
FIG. 4 is an exploded perspective view of the first sole structure.

An article of footwear 10 is depicted in FIGS. 1 and 2 as including an upper 20 and a sole structure 30. For reference purposes, footwear 10 may be divided into three general regions: a forefoot region 11, a midfoot region 12, and a heel region 13, as shown in FIGS. 1 and 2. Footwear 10 also includes a lateral side 14 and a medial side 15. Forefoot region 11 generally includes portions of footwear 10 corresponding with the toes and the joints connecting the metatarsals with the phalanges. Midfoot region 12 generally includes portions of footwear 10 corresponding with the arch area of the foot, and heel region 13 corresponds with rear portions of the foot, including the calcaneus bone. Lateral side 14 and medial side 15 extend through each of regions 11-13 and correspond with opposite sides of footwear 10. Regions 11-13 and sides 14-15 are not intended to demarcate precise areas of footwear 10. Rather, regions 11-13 and sides 14-15 are intended to represent general areas of footwear 10 to aid in the following discussion. In addition to footwear 10, regions 11-13 and sides 14-15 may also be applied to upper 20, sole structure 30, and individual elements thereof.

Upper 20 is depicted as having a substantially conventional configuration incorporating a plurality material elements (e.g., textiles, foam, leather, and synthetic leather) that are stitched or adhesively bonded together to form an interior void for securely and comfortably receiving a foot. The material elements may be selected and located with respect to upper 20 in order to selectively impart properties of durability, air-permeability, wear-resistance, flexibility, and comfort, for example. An ankle opening 21 in heel region 13 provides access to the interior void. In addition, upper 20 may include a lace 22 that is utilized in a conventional manner to modify the dimensions of the interior void, thereby securing the foot within the interior void and facilitating entry and removal of the foot from the interior void. Lace 22 may extend through apertures in upper 20, and a tongue portion of upper 20 may extend between the interior void and lace 22. Given that various aspects of the present application primarily relate to sole structure 30, upper 20 may exhibit the general configuration discussed above or the general configuration of practically any other conventional or non-conventional upper. Accordingly, the overall structure of upper 20 may vary significantly.

Sole structure 30 is secured to upper 20 and has a configuration that extends between upper 20 and the ground. In addition to attenuating ground reaction forces (i.e., providing cushioning for the foot), sole structure 30 may provide traction, impart stability, and limit various foot motions, such as pronation. In addition to the various elements discussed in detail below, sole structure 30 may incorporate one or more support members, moderators, or reinforcing structures, for example, that further enhance the ground reaction force attenuation characteristics of sole structure 30 or the performance properties of footwear 10. Sole structure 30 may also incorporate an insole or sockliner that is located within the void in upper 20 and adjacent a plantar (i.e., lower) surface of the foot to enhance the comfort of footwear 10. As alternatives, either of a sole structure 30a and a sole structure 30b, which are discussed below following a discussion of sole structure 30, may also be utilized with upper 20.

First Sole Structure Configuration

The primary elements of sole structure 30 are a plate 40, a chamber 50, and an outsole 60, as depicted in FIGS. 3-8. Plate 40 forms an upper portion of sole structure 30 and is positioned adjacent to upper 20. Chamber 50 forms a middle portion of sole structure 30 and is positioned between plate 40 and outsole 60. In addition, outsole 60 forms a lower portion of sole structure 30 and is positioned to engage the ground. Each of plate 40, chamber 50, and outsole 60 extend around a perimeter of sole structure 30 and have a shape that generally corresponds with an outline of the foot. More particularly, plate 40, chamber 50, and outsole 60 extend from forefoot region 11 to heel region 13 and also from lateral side 14 to medial side 15. Accordingly, each of plate 40, chamber 50, and outsole 60 are exposed to an exterior of footwear 10 and cooperatively form a side surface of sole structure 30. In further configurations, however, upper 20 may extend over the sides of plate 40, edges of plate 40 may be spaced inward from the side surface of sole structure 30, or portions of plate 40 and outsole 60 may cover the sides of chamber 50, for example.

Figure 9:
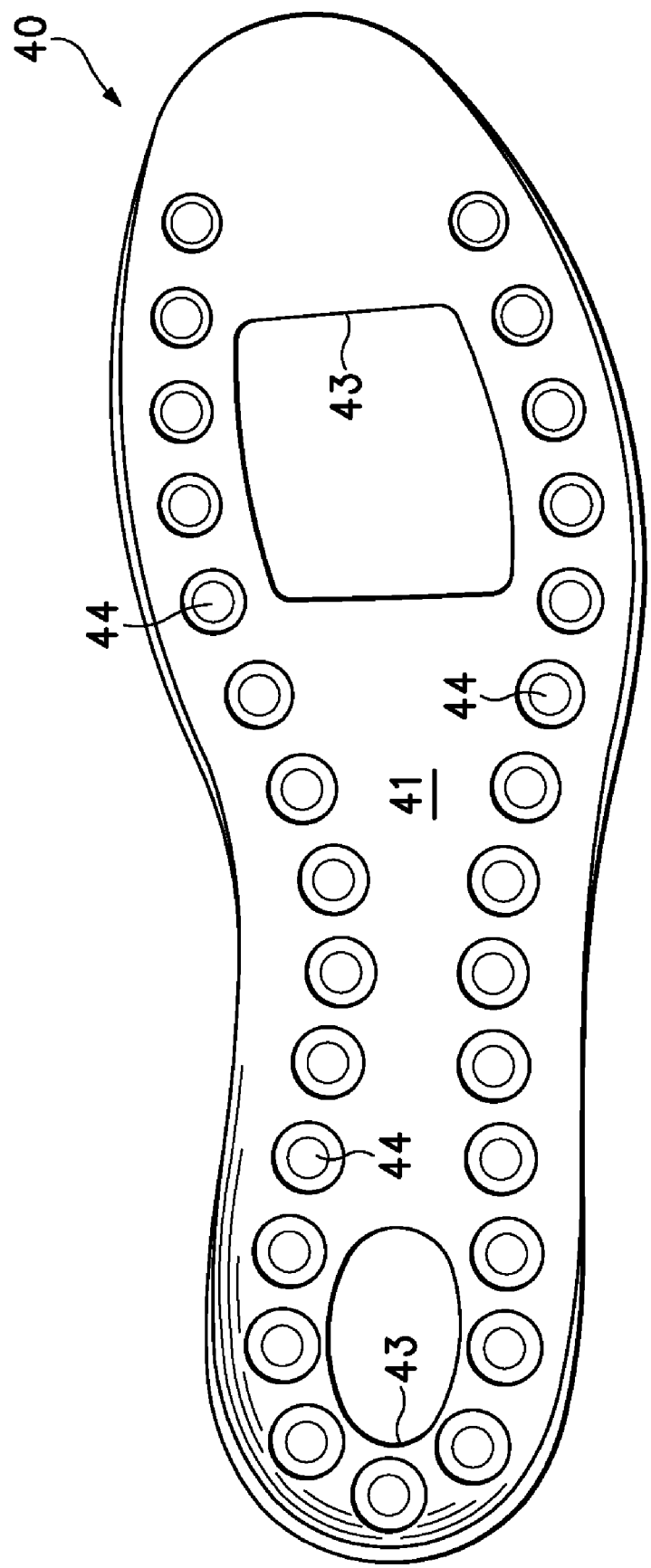
FIG. 9 is a top plan view of a plate of the first sole structure.
Figure 10:
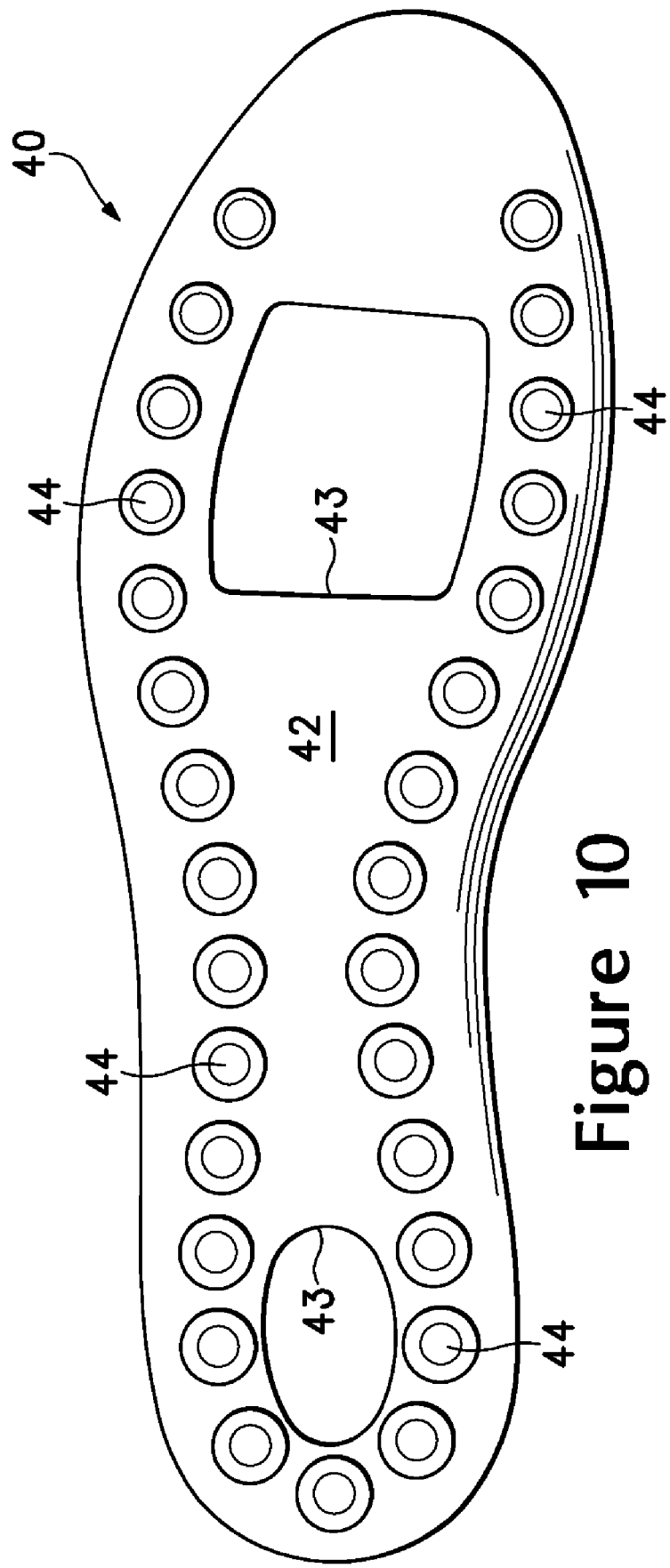
FIG. 10 is a bottom plan view of the plate of the first sole structure.

Plate 40 and has an upper surface 41 and an opposite lower surface 42, as depicted in FIGS. 9 and 10. Two apertures 43 extend between surfaces 41 and 42 to form openings that expose portions of chamber 50. One of apertures 43 is primarily located in forefoot region 11 and extends into midfoot region 12, and the other of apertures 43 is located in heel region 13 and at a position that corresponds with a calcaneus bone of the foot. That is, the aperture 43 in heel region 13 is generally located to correspond with the heel of the foot. Whereas upper surface 41 has a generally smooth aspect that is contoured to conform with the general anatomical structure of the foot, lower surface 42 defines a plurality of downwardly-extending projections 44 that extend into depressions in chamber 50.

Each of projections 44 are depicted as having a generally circular shape that tapers as each of projections 44 extend away from lower surface 42. In addition, lower surfaces of projections 44 are depicted as being flat. In further configurations, projections 44 may be triangular, square, rectangular, or any other regular or non-regular shape, and the lower surface may be curved or non-planar. In some configurations, the various projections 44 may each exhibit different shapes or lengths. Upper surface 41 forms depressions that extend downward and into projections 44, thereby imparting a generally hollow aspect to projections 44, but projections 44 may also be solid. Accordingly, the specific configuration of the various projections 44 may vary.

Plate 40 may be manufactured from a diverse range of materials that include polymers and metals, for example. Suitable polymers include polyester, thermoset urethane, thermoplastic urethane, various nylon formulations, rubber, polyether block amide, polybutylene terephthalate, or blends of these materials. Composite materials may also be formed by incorporating glass fibers or carbon fibers into the various polymer materials discussed above. Suitable metals may include steel, aluminum, or titanium, and in some configurations metals may be combined with polymers. In some configurations, plate 40 may also be formed from polymer foam materials. Accordingly, a variety of different materials may be utilized in manufacturing plate 40, depending upon the desired properties for sole structure 30.

Figure 11:
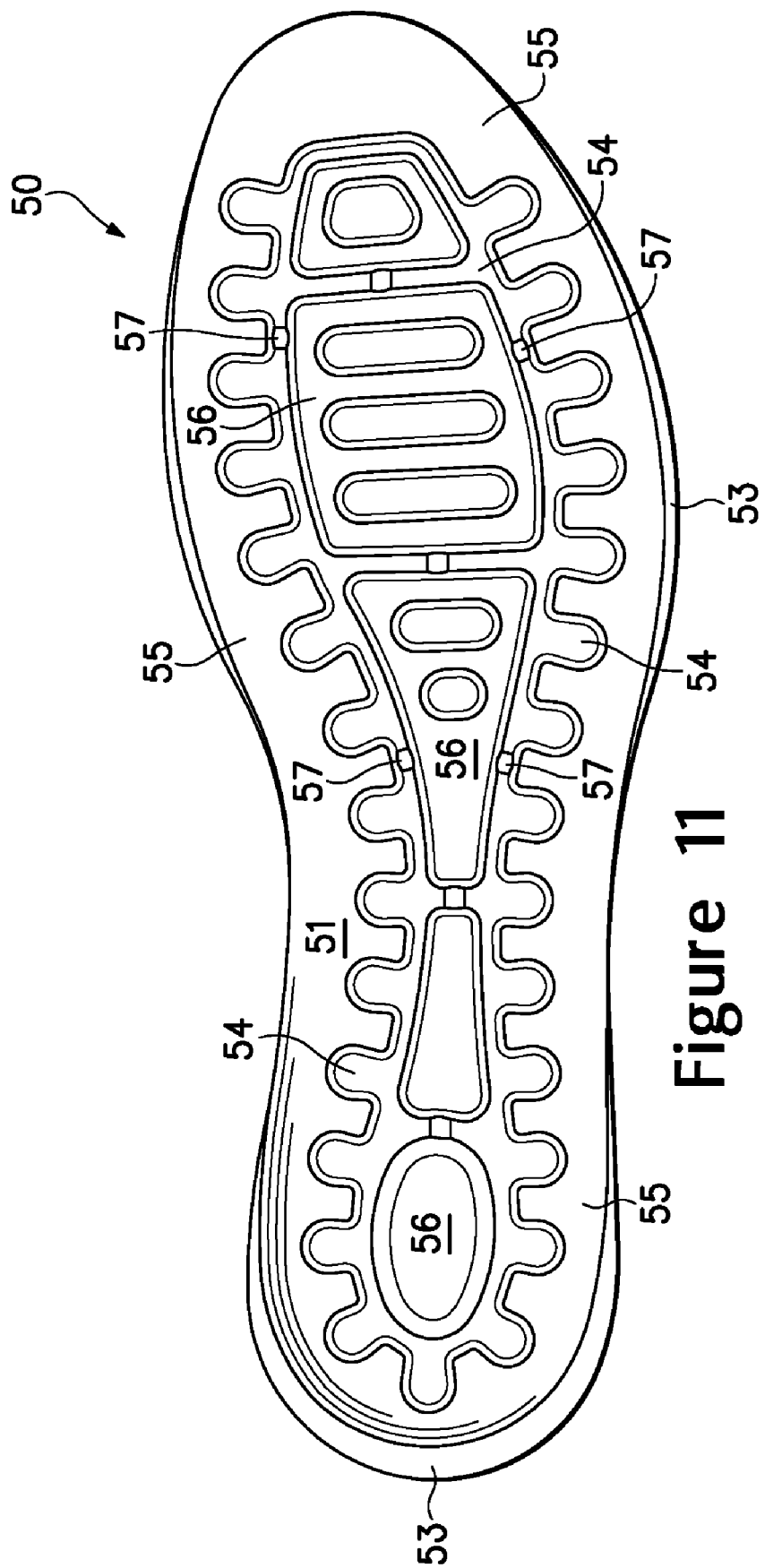
FIG. 11 is a top plan view of a chamber of the first sole structure.
Figure 12:
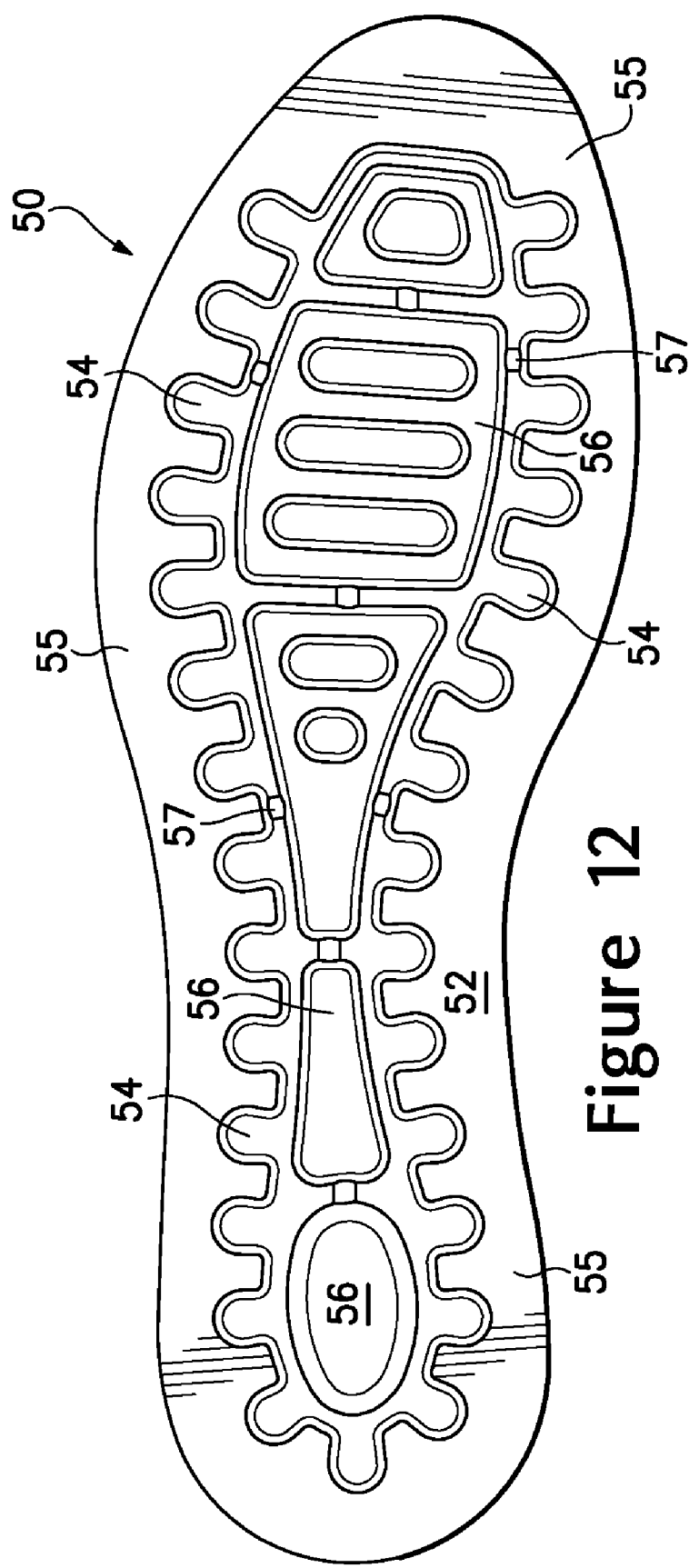
FIG. 12 is a bottom plan view of the chamber of the first sole structure.

Chamber 50, which is depicted individually in FIGS. 11 and 12, is formed from a polymer material that provides a sealed barrier for enclosing a fluid. The polymer material defines an upper surface 51, an opposite lower surface 52, and a sidewall surface 53 that extends around a periphery of chamber 50 and between surfaces 51 and 52. As discussed above, chamber 50 has a shape that generally corresponds with an outline of the foot. As with plate 40 and outsole 60, chamber 50 is exposed to an exterior of footwear 10 and forms a portion of the side surface of sole structure 30. More particularly, sidewall surface 53 is exposed to the exterior of footwear 10. In comparison with plate 40 and outsole 60, however, sidewall surface 53 is depicted as forming a majority of the side surface.

In addition to having a shape that generally corresponds with an outline of the foot, surfaces 51 and 52 are contoured in a manner that is suitable for footwear applications. With reference to FIGS. 1-2 and 7-8, chamber 50 exhibits a tapered configuration between heel region 13 and forefoot region 11. That is, the portion of chamber 50 in heel region 13 exhibits a greater overall thickness than the portion of chamber 50 in forefoot region 11. The tapering leads chamber 50 to have a configuration wherein the portion of upper surface 51 in heel region 13 is generally at a greater elevation than the portion of upper surface 51 in forefoot region 11. The tapering of chamber 50 and the resulting differences in elevations impart an overall contour to chamber 50 that complements the general anatomical structure of the foot. That is, these contours ensure that the heel of the foot is slightly raised in relation to the forefoot. Although not depicted in the figures, some configurations of chamber 50 may include a depression in heel region 13 for receiving the heel, and chamber 50 may have a protrusion in midfoot region 12 that supports the arch of the foot.

Chamber 50 includes various bonded areas 54 where upper surface 51 is bonded or otherwise joined to lower surface 52. In general, bonded areas 54 are spaced inward from sidewall surface 53 and form various depressions or indentations in each of surfaces 51 and 52. The depressions in upper surface 51 are shaped to receive the various projections 44 that extend downward from plate 40. That is, projections 44 extend into the depressions formed by portions of bonded area 54. Similarly, the depressions in lower surface 52 receive upwardly-extending portions of outsole 60, as discussed in greater detail below. In addition to forming depressions or indentations in surfaces 51 and 52, bonded areas 54 also define a peripheral subchamber 55 and a central subchamber 56 in chamber 50.

Peripheral subchamber 55 extends around the periphery of chamber 50 and is, therefore, partially formed by sidewall surface 53. Given that peripheral subchamber 55 has a generally U-shaped configuration, central subchamber 56 is centrally-located within peripheral subchamber 55. When sole structure 30 is compressed between the foot and the ground during various ambulatory activities, such as running and walking, chamber 50 is also compressed such that the fluid within chamber 50 may pass between subchambers 55 and 56. More particularly, the fluid within chamber 50 may pass through various conduits 57 that extend between subchambers 55 and 56. In some configurations, conduits 57 may be absent or sealed to prevent fluid transfer between subchambers 55 and 56. When conduits 57 are absent or sealed, the fluid within subchambers 55 and 56 may be pressurized to different degrees. As an example, central subchamber 56 may have an ambient pressure that compresses upon pressure from the foot, whereas peripheral subchamber 55 has a greater than ambient pressure that provides support to the periphery of sole structure 30. In some configurations, sidewall surface 53 may be absent from chamber 50 to expose the interior of peripheral subchamber 55, but central subchamber 56 may remain sealed at an ambient or greater fluid pressure.

Figure 6A:
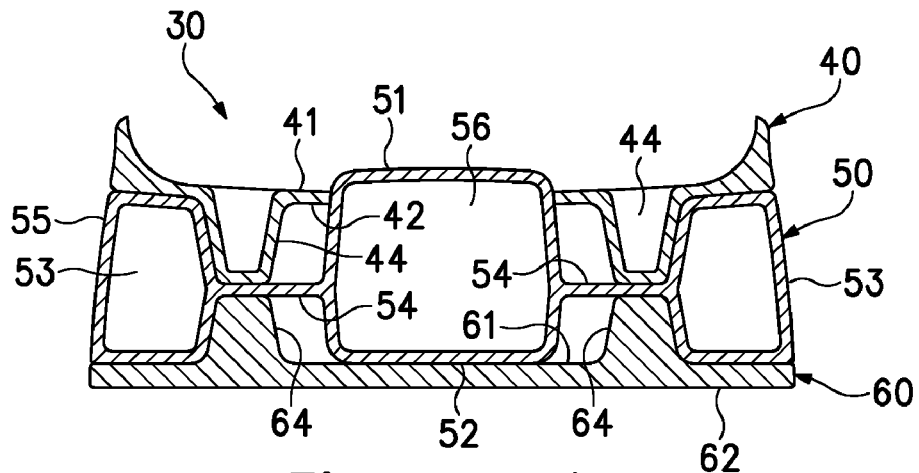
FIGS. 6A-6C are cross-sectional views of the first sole structure, as defined by section lines 6A-6C in FIG. 5.
Figure 6B:
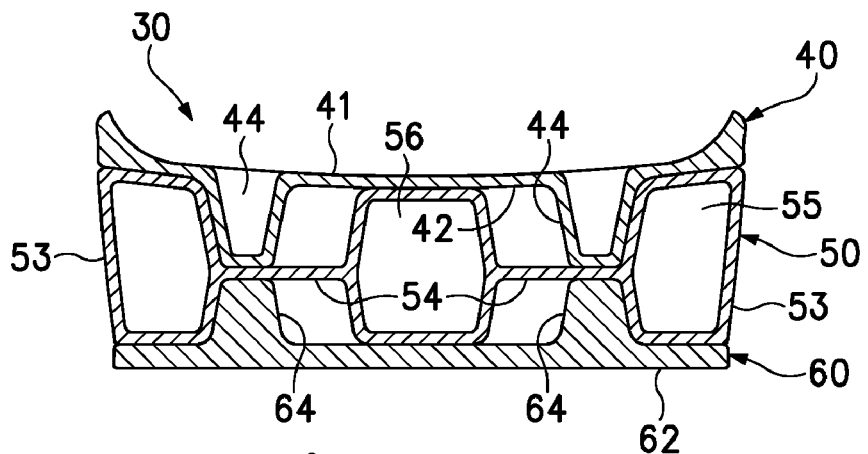
Figure 6C:
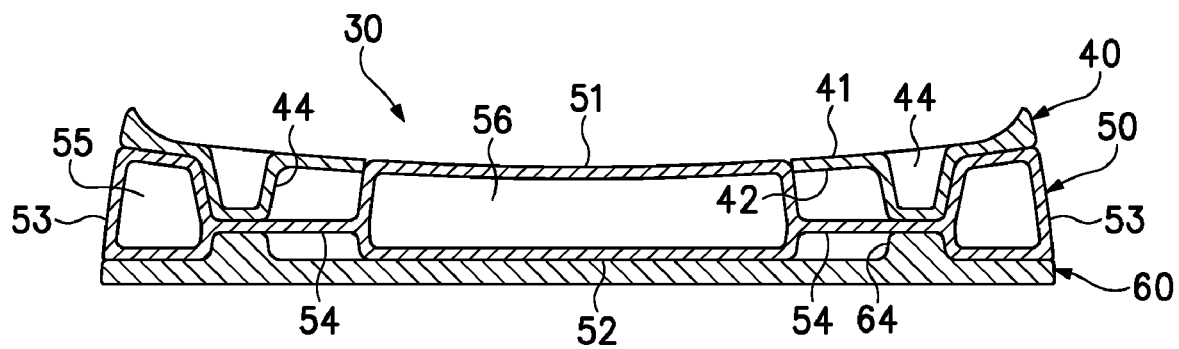
Figure 7:
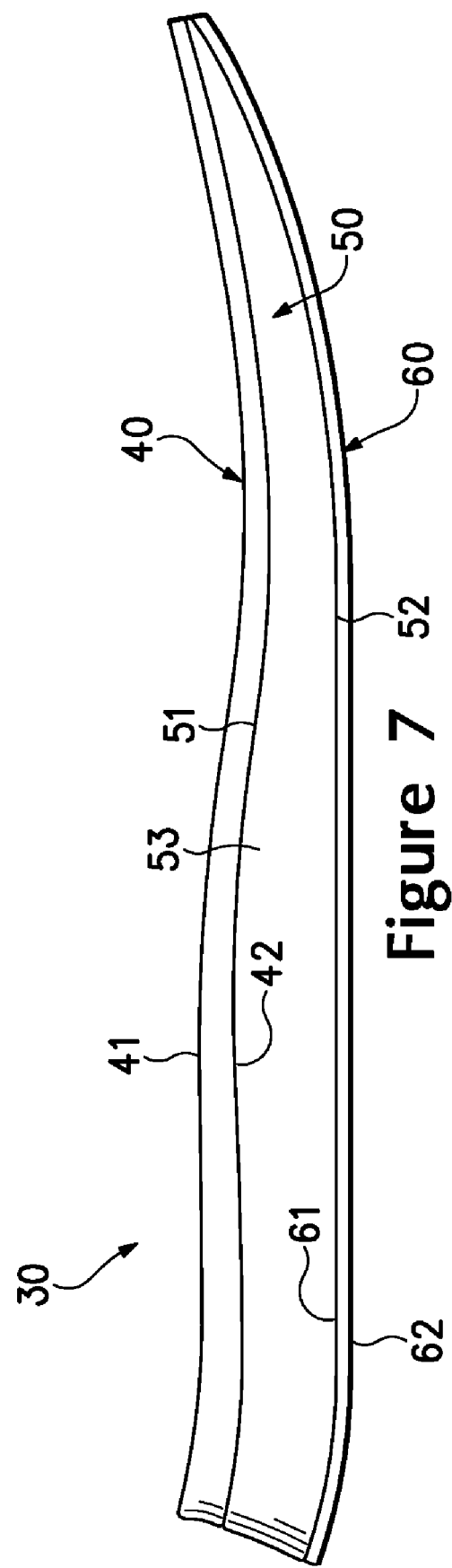
FIG. 7 is a lateral side elevational view of the first sole structure.
Figure 8:
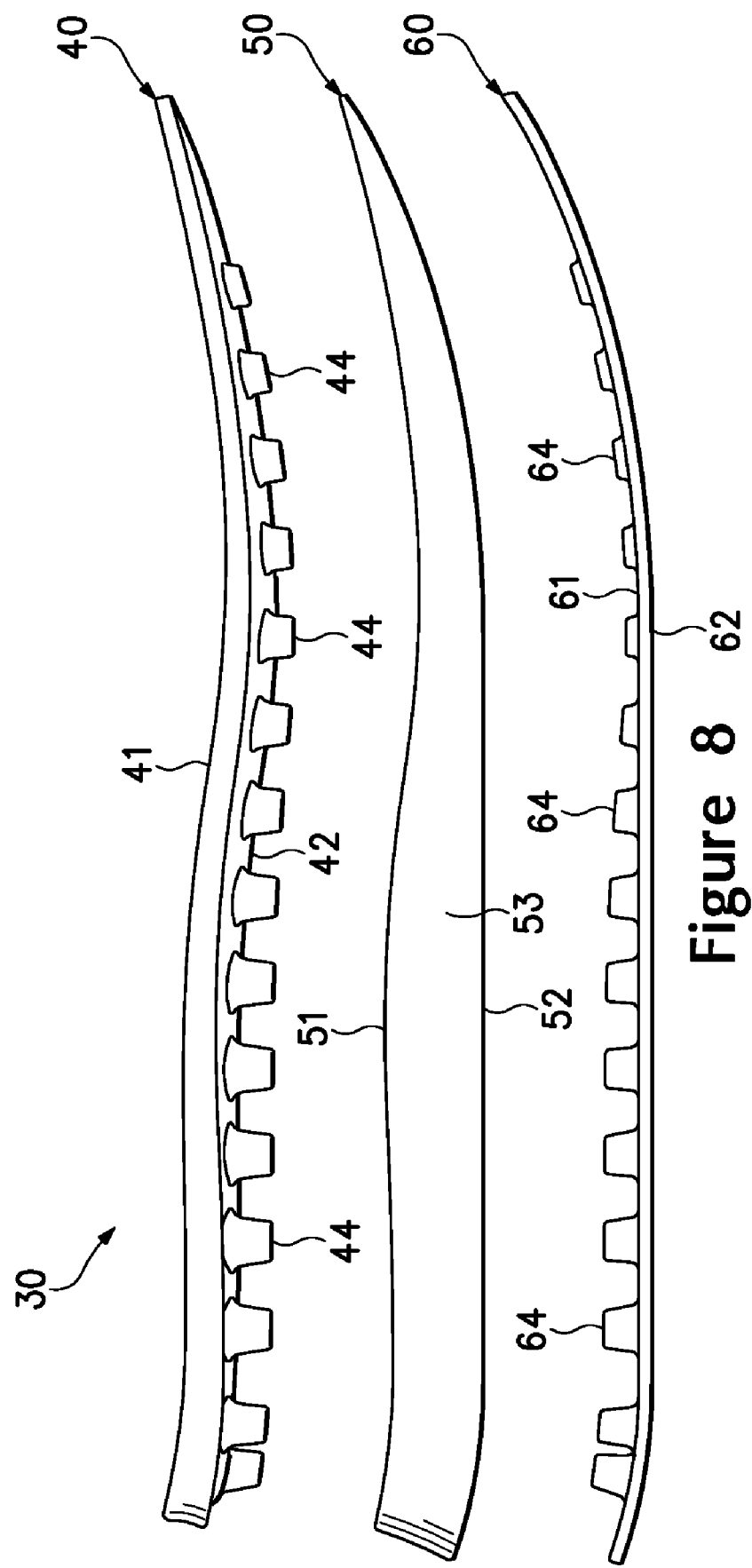
FIG. 8 is an exploded lateral side elevational view of the first sole structure.

Bonded areas 54 extend into central subchamber 56 and further subdivide central subchamber 56. As noted above, plate 40 defines two apertures 43. A portion of central subchamber 56 is located in forefoot region 11 and has a generally square configuration that extends into one of apertures 43, and another portion of central subchamber 56 is located in heel region 13 and has an elliptical configuration that extends into the other one of apertures 43. Other portions of central subchamber 56 are covered by plate 40. Referring to FIG. 6A, the portion of central subchamber 56 located in heel region 13 extends above upper surface 41. In contrast, and as shown in FIG. 6C, the portion of central subchamber 56 located in forefoot region 11 is generally flush with upper surface 41. In further configurations, the various portions of central subchamber 56 may be either flush, above, or below the areas of upper surface 41 that form apertures 43.

The fluid within chamber 50 may range in pressure from zero to three-hundred-fifty kilopascals (i.e., approximately fifty-one pounds per square inch) or more. Given the configuration of sole structure 30 depicted in the figures, a suitable pressure for the fluid is a substantially ambient pressure. That is, the pressure of the fluid may be within five kilopascals of the ambient pressure of the air surrounding footwear 10. In addition to air and nitrogen, the fluid contained by chamber 50 may include octafluorapropane or be any of the gasses disclosed in U.S. Pat. No. 4,340,626 to Rudy, such as hexafluoroethane and sulfur hexafluoride, for example. In some configurations, chamber 50 may incorporate a valve that permits the individual to adjust the pressure of the fluid. In other configurations, chamber 50 may be incorporated into a fluid system, as disclosed in U.S. Pat. No. 7,210,249 to Passke, et al., as a pump chamber or a pressure chamber. In order to pressurize chamber 50 or portions of chamber 50, the general inflation method disclosed in U.S. patent application Ser. No. 11/957,633 (entitled Method For Inflating A Fluid-Filled Chamber and filed in the U.S. Patent and Trademark Office on 17 Dec. 2007), which is incorporated herein by reference, may be utilized.

A wide range of polymer materials may be utilized for chamber 50. In selecting materials for chamber 50, engineering properties of the material (e.g., tensile strength, stretch properties, fatigue characteristics, dynamic modulus, and loss tangent) as well as the ability of the material to prevent the diffusion of the fluid contained by chamber 50 may be considered. When formed of thermoplastic urethane, for example, the outer barrier of chamber 50 may have a thickness of approximately 1.0 millimeter, but the thickness may range from 0.25 to 2.0 millimeters or more, for example. In addition to thermoplastic urethane, examples of polymer materials that may be suitable for chamber 50 include polyurethane, polyester, polyester polyurethane, and polyether polyurethane. Chamber 50 may also be formed from a material that includes alternating layers of thermoplastic polyurethane and ethylene-vinyl alcohol copolymer, as disclosed in U.S. Pat. Nos. 5,713,141 and 5,952,065 to Mitchell, et al. A variation upon this material may also be utilized, wherein a center layer is formed of ethylene-vinyl alcohol copolymer, layers adjacent to the center layer are formed of thermoplastic polyurethane, and outer layers are formed of a regrind material of thermoplastic polyurethane and ethylene-vinyl alcohol copolymer. Another suitable material for chamber 50 is a flexible microlayer membrane that includes alternating layers of a gas barrier material and an elastomeric material, as disclosed in U.S. Pat. Nos. 6,082,025 and 6,127,026 to Bonk, et al. Additional suitable materials are disclosed in U.S. Pat. Nos. 4,183,156 and 4,219,945 to Rudy. Further suitable materials include thermoplastic films containing a crystalline material, as disclosed in U.S. Pat. Nos. 4,936,029 and 5,042,176 to Rudy, and polyurethane including a polyester polyol, as disclosed in U.S. Pat. Nos. 6,013,340; 6,203,868; and 6,321,465 to Bonk, et al.

Outsole 60, which is depicted individually in FIG. 13, forms the ground-contacting portion of footwear 10. Outsole 60 has an upper surface 61 and an opposite lower surface 62. Upper surface 61 defines a plurality of upwardly-extending projections 64 that extend into bonded areas 54 in lower surface 52 of chamber 50. As discussed above, bonded areas 54 form various depressions or indentations in each of surfaces 51 and 52. Whereas the depressions in upper surface 51 receive the various projections 44 that extend downward from plate 40, the depressions in lower surface 52 receive projections 64. Although a variety of materials may be utilized for outsole 60, rubber materials may be utilized to impart durability and wear-resistance. Lower surface 62 may also be textured to enhance the traction (i.e., friction) properties between footwear 10 and the ground.

Each of projections 64 are depicted as having a generally circular shape that tapers as each of projections 64 extend away from upper surface 61. In addition, upper surfaces of projections 64 are depicted as being flat. In further configurations, projections 64 may be triangular, square, rectangular, or any other regular or non-regular shape, and the lower surface may be curved or non-planar. In some configurations, the various projections 64 may each exhibit different shapes or lengths. Unlike projections 44, projections 64 are not depicted as being hollow, but may be hollow in some configurations. Accordingly, the specific configuration of the various projections 64 may vary.

A variety of techniques may be utilized to manufacture sole structure 30. As an example, chamber 50 may be formed from a pair of polymer sheets that are molded and bonded during a thermoforming process. More particularly, the thermoforming process (a) imparts shape to one of the polymer sheets in order to form upper surface 51, (b) imparts shape to the other of the polymer sheets in order to form lower surface 52, (c) forms sidewall surface 53 from one or both of the sheets, and (d) forms bonded areas 54 to join interior portions of surfaces 41 and 42. Once chamber 50 is formed, each of plate 40 and outsole 60 are secured to opposite sides of chamber 50, through adhesive bonding or heat bonding, for example. Chamber 50 may also be formed from a blowmolding process wherein a parison or molten or uncured polymer material extends between mold portions having a shape of chamber 50. The polymer material is then drawn into the mold to impart the shape of chamber 50. Upon cooling or curing, chamber 50 is removed from the mold and each of plate 40 and outsole 60 are secured to opposite sides of chamber 50.

Based upon the discussion above, sole structure 30 has a configuration wherein different elements of sole structure 30 impart performance characteristics (e.g., support the foot, provide ground reaction force attenuation, impart stability, or limit foot motions) in different areas of sole structure 30. More particularly, chamber 50 and the fluid within chamber 50 are primarily responsible for supporting the foot and providing force attenuation in central areas of sole structure 30. Around the periphery of sole structure 30, the fluid is absent in the areas where projections 44 and 64 extend into chamber 50. That is, projections 44 and 64 support the foot, provide force attenuation, impart stability, or limit foot motions around portions of the periphery of sole structure 30. In areas where the fluid is absent through all or a substantially portion of the thickness of sole structure 30, therefore, plate 40 and outsole 60 may be primarily responsible for imparting performance characteristics to sole structure 30.

Variations of the First Sole Structure

The properties of plate 40, chamber 50, and outsole 60 have an effect upon the performance characteristics of footwear 10. That is, the shape and dimensions of plate 40, chamber 50, and outsole 60 (e.g., thickness and contour) and the materials that form plate 40, chamber 50, and outsole 60 may affect the degree to which sole structure 30 attenuates ground reaction forces, imparts stability, and limits foot motions, for example. By varying the shape, dimensions, or materials of plate 40, chamber 50, and outsole 60, therefore, the performance characteristics of footwear 10 may be altered. That is, footwear 10 may be manufactured for different athletic activities by modifying the shape, dimensions, or materials of one or more of plate 40, chamber 50, and outsole 60. Examples of variations in the components of sole structure 30 include, for example, the number and locations of projections 44 and 64, the materials forming plate 40 and outsole 60, the thickness of plate 40, the locations and size of apertures 43

In manufacturing sole structure 30 and the sole structures for other articles of footwear, components having the general configurations of plate 40, chamber 50, and outsole 60 may be utilized. As discussed above, the configuration of sole structure 30 depicted in the figures may be suitable for running. When plate 40 is formed from a material having greater stiffness or with different configurations for apertures 43, for example, the resulting sole structure may be more suitable for other athletic activities, such as basketball or tennis. Similarly, by changing the fluid pressure within chamber 50 or the thickness of outsole 60, for example, the resulting sole structure may be suitable for other athletic activities. Accordingly, by modifying the properties of one component of sole structure 30, the resulting sole structure may be suitable for a different athletic activity.

Figure 14A:
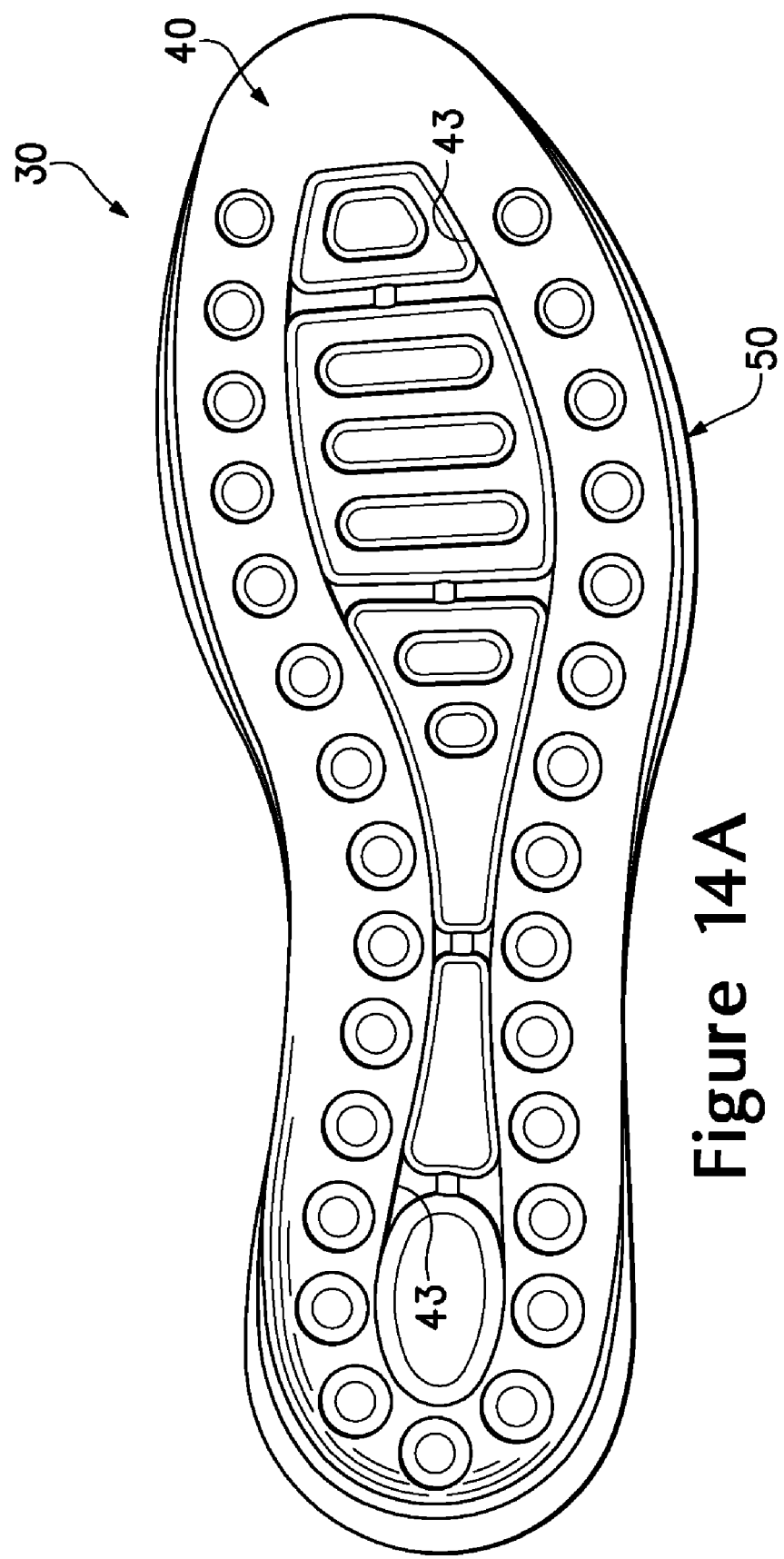
FIGS. 14A-14G are top plan views corresponding with FIG. 5 and depicting further configurations of the first sole structure.
Figure 14B:
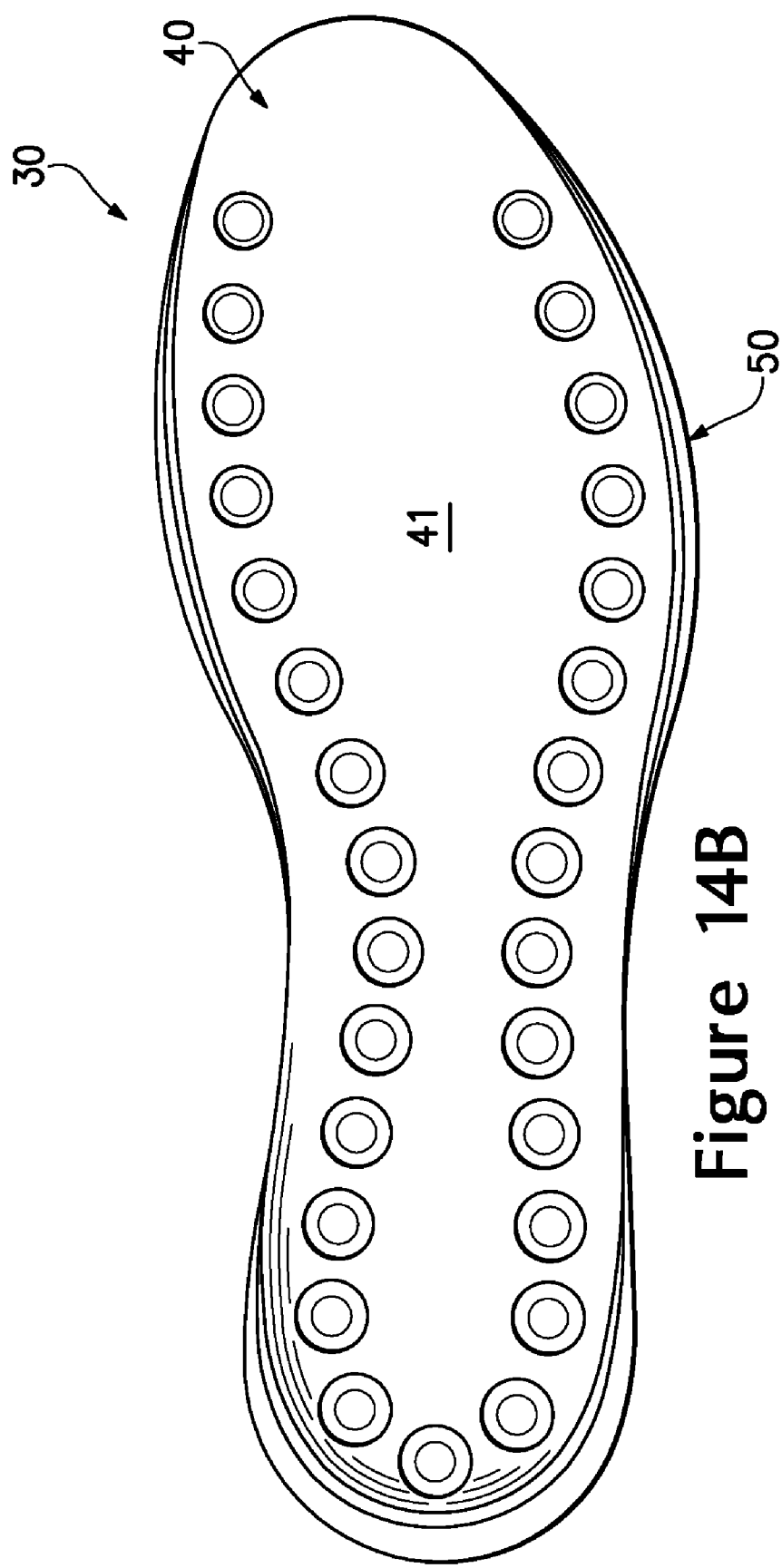
Figure 14C:
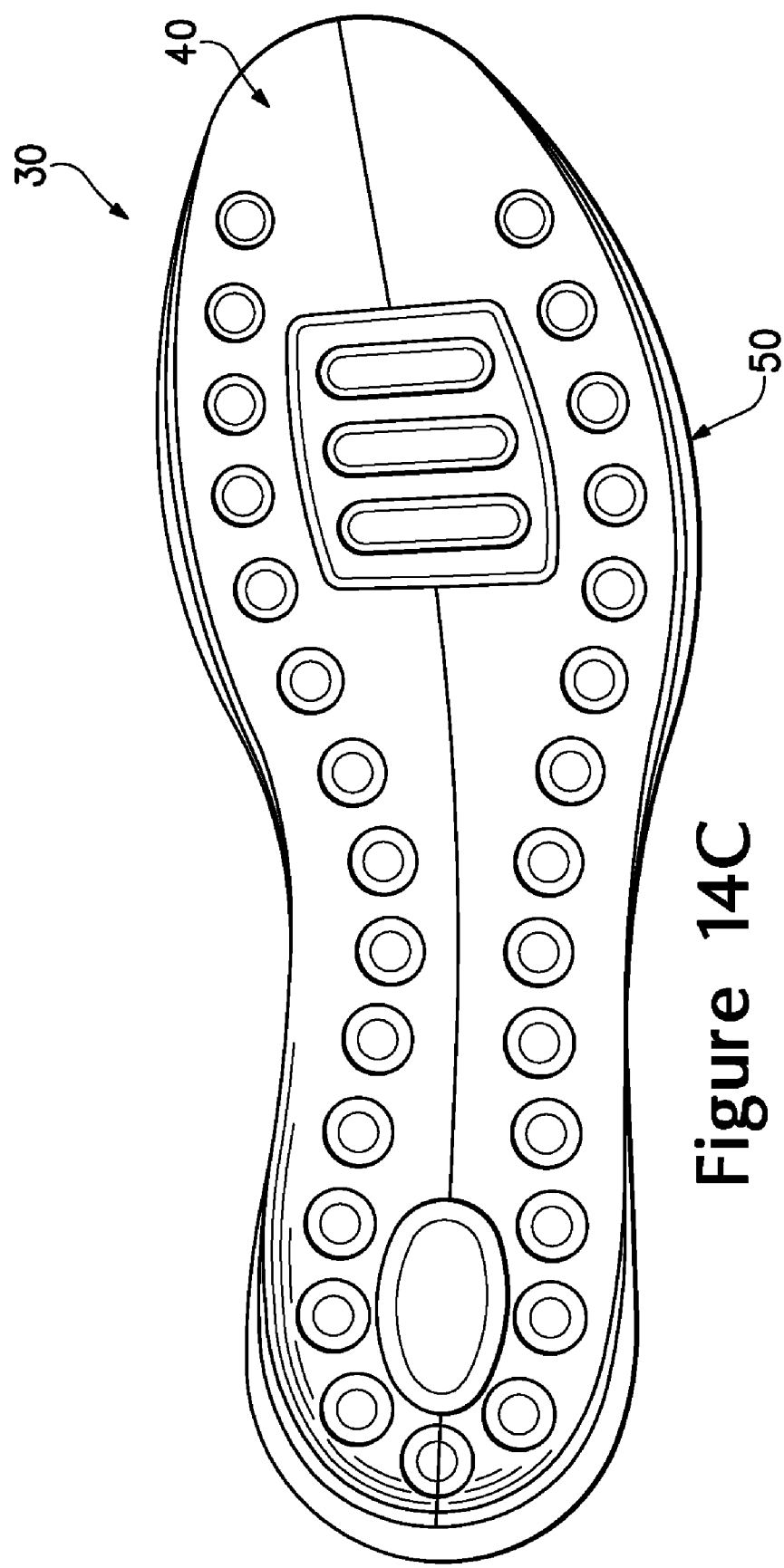

A variety of modifications may be made to plate 40, chamber 50, and outsole 60 in order to vary the resulting properties of sole structure 30. With reference to FIG. 14A, plate 40 is depicted as having a single aperture 43 that extends from forefoot region 11 to heel region 13, which may increase the overall flexibility of sole structure 30. As a comparison, FIG. 14B depicts a configuration wherein plate 40 does not include any apertures 43, which may decrease the flexibility of sole structure 30. Although the entirety of plate 40 may be formed from a single material, FIG. 14C depicts a configuration wherein lateral side 14 is formed from a different material than medial side 15. If, for example, the material of lateral side 14 is more flexible than the material of medial side 15, then sole structure 30 may limit the degree to which the foot pronates or rolls from the lateral to medial side during running.

Figure 14D:
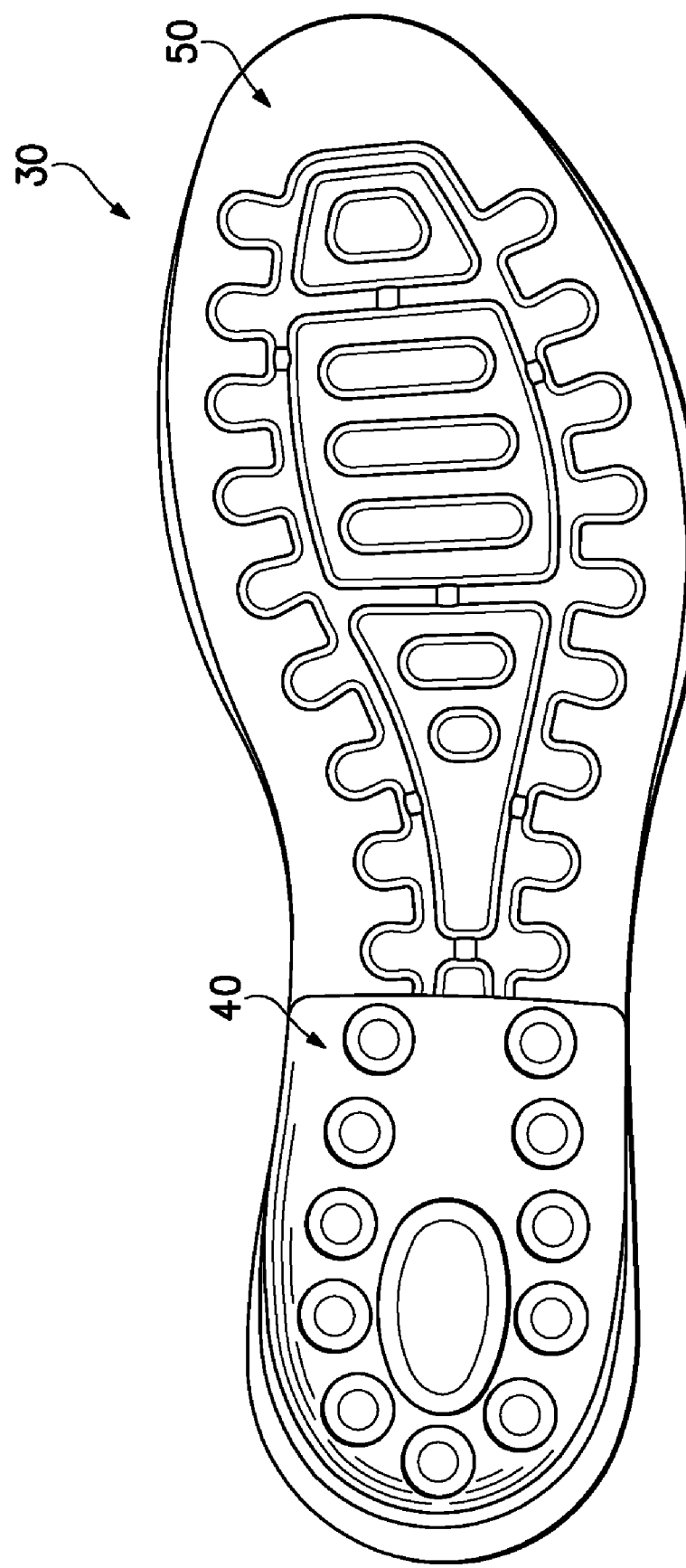
Figure 14E:
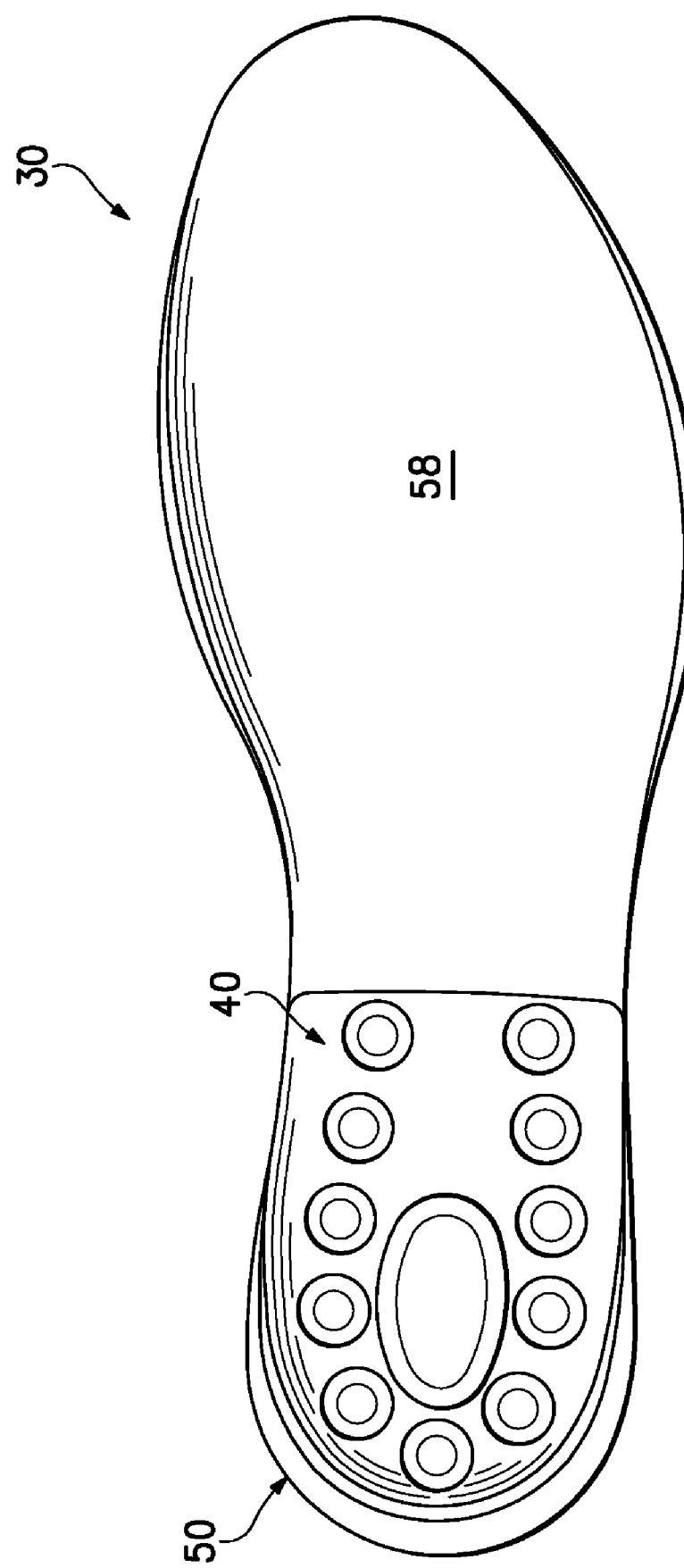
Figure 14F:
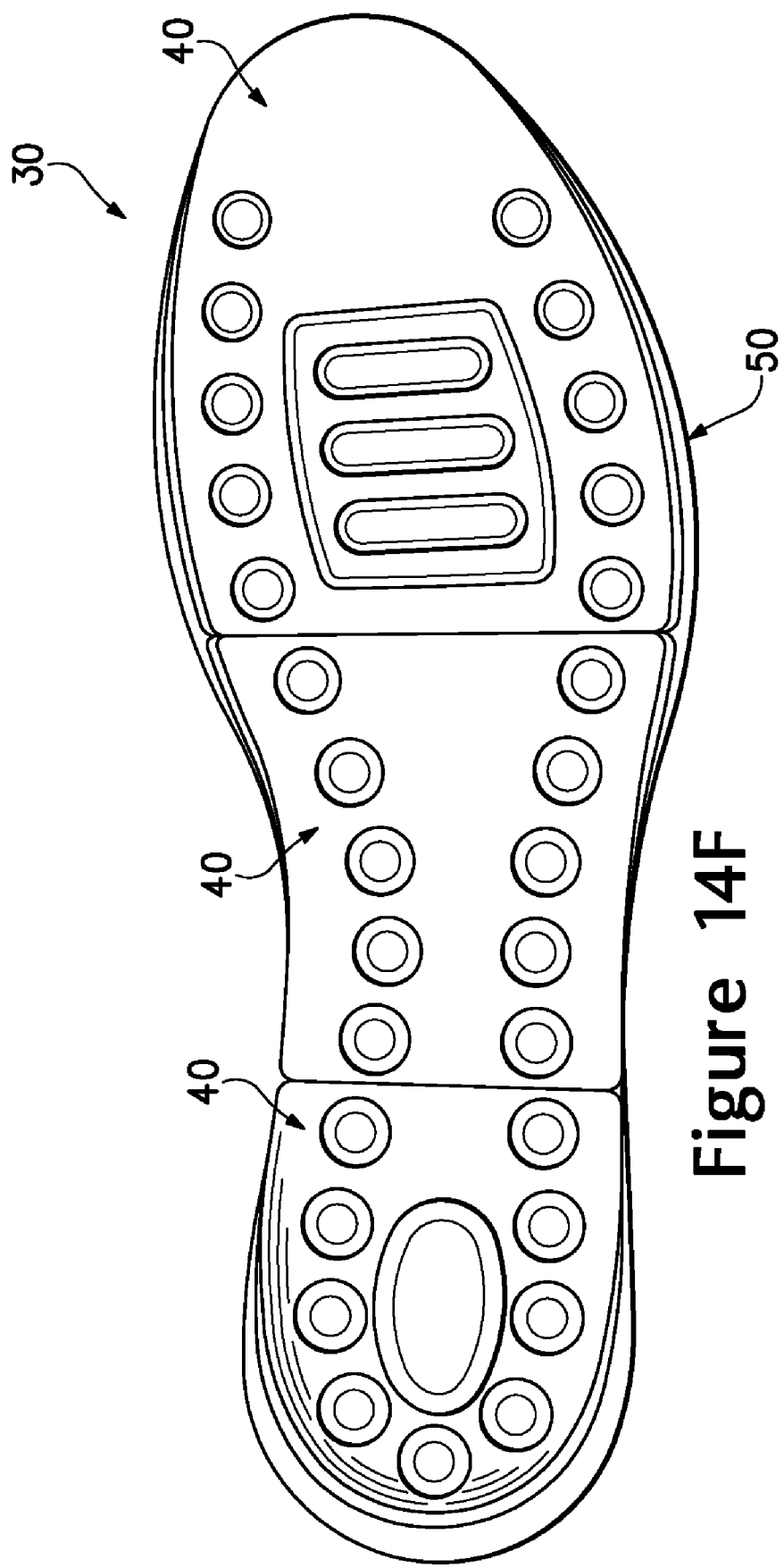
Figure 14G:
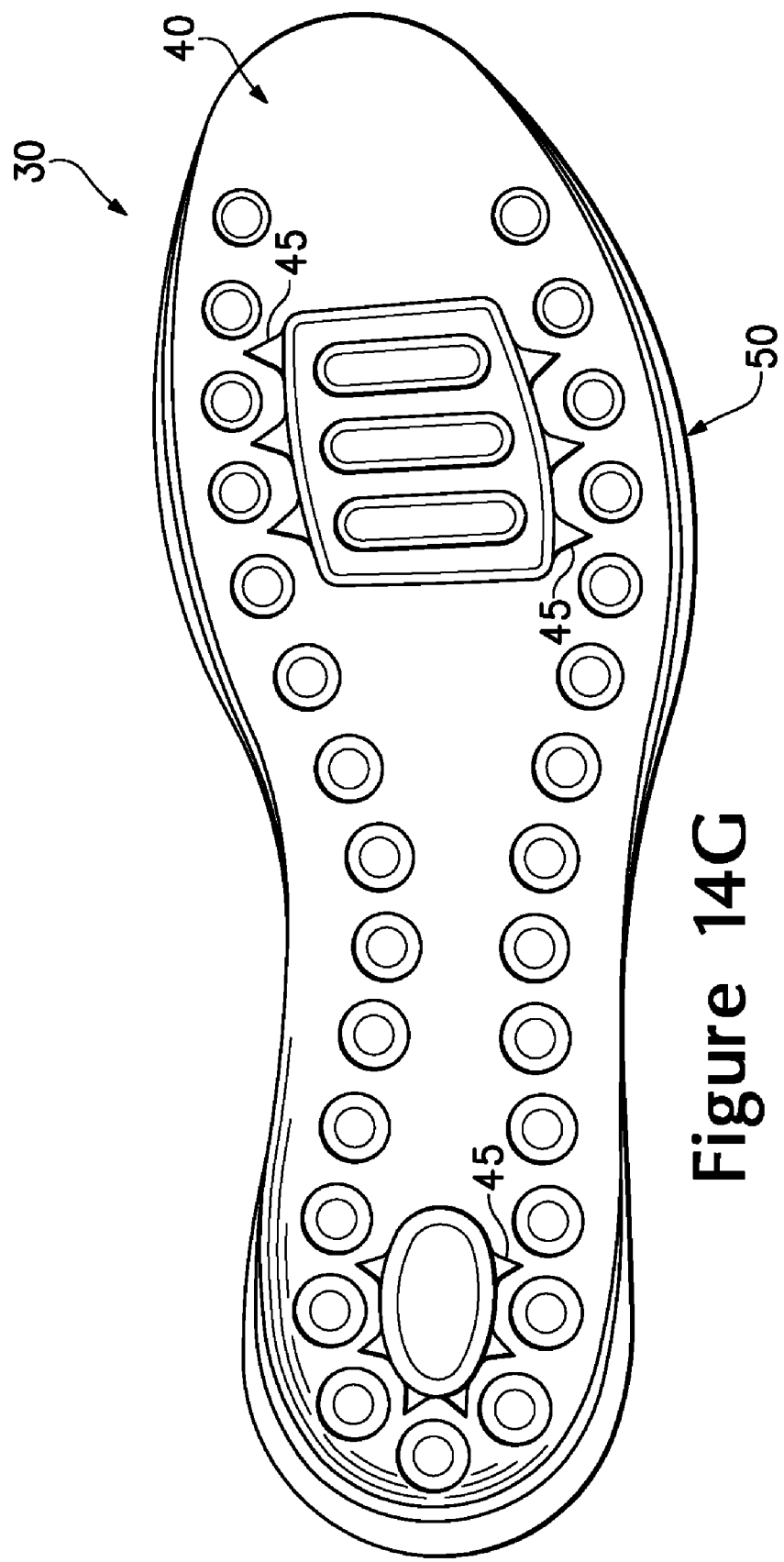

Plate 40 is discussed above as extending throughout the length and width of sole structure 30, but may be limited to heel region 13 and rearward portions of midfoot region 12, as depicted in FIG. 14D. As a further alternative, plate 40, chamber 50, and outsole 60 may be limited to heel region 13, as depicted in FIG. 14E, and a remainder of sole structure 30 may be formed from a polymer foam element. In some configurations, plate 40 may have a segmented or non-continuous configuration that effectively forms multiple plates, as depicted in FIG. 14F. In comparison with the areas where plate 40 is present, the areas where plate 40 is segmented may have greater flexibility, thereby forming flexion lines across the width of sole structure 30. Another manner of enhancing the flexibility of sole structure 30 is to form notches 45 or other structures in selected portion of plate 40, as depicted in FIG. 14G.

Figure 15A:
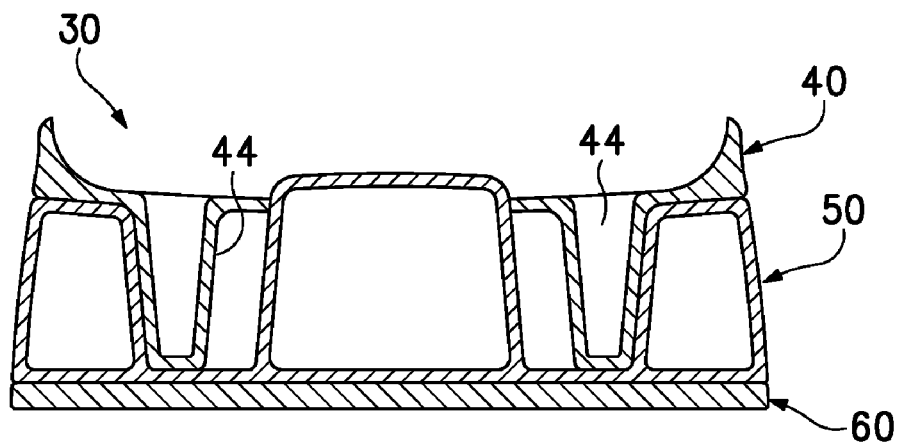
FIGS. 15A-15F are cross-sectional views corresponding with FIG. 6A and depicting further configurations of the first sole structure.
Figure 15B:
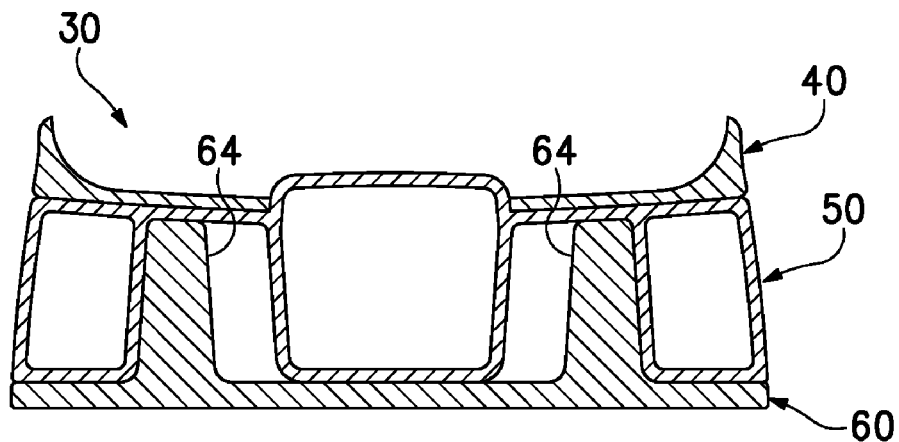
Figure 15C:
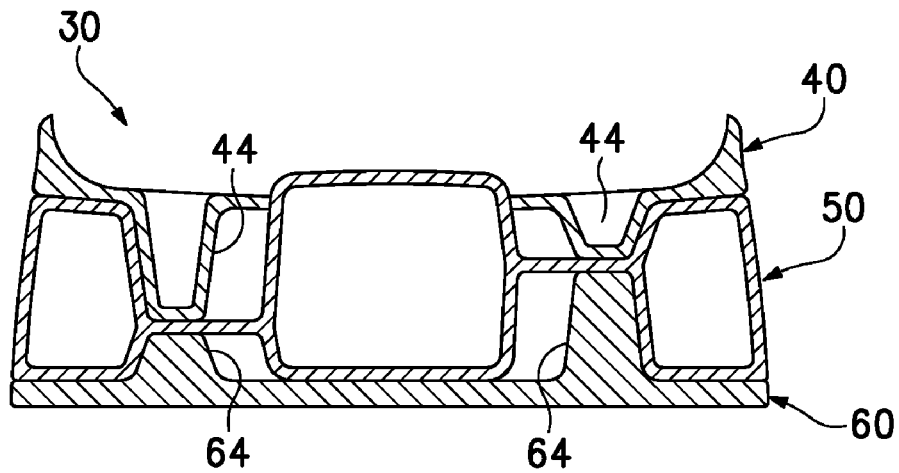
Figure 15D:
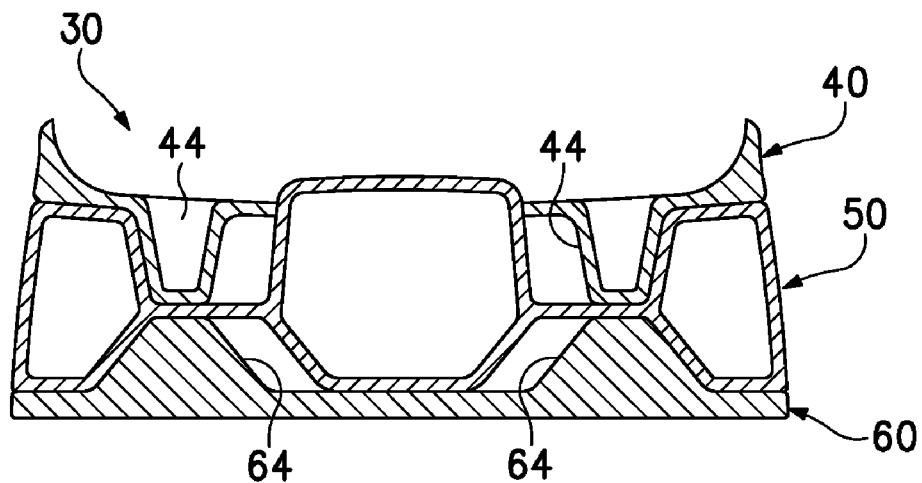

Plate 40 and outsole 60 may be formed from different materials, which have an effect upon the relative compressibilities of projections 44 and 64. FIGS. 6A-6C depict a configuration wherein projections 44 and 64 each extend to an approximate midpoint of the thickness of chamber 50. In other configurations, however, projections 44 and 64 may extend to different locations. Referring to FIG. 15A, projections 44 extend through a majority of the thickness of chamber 50. If the material of plate 40 is less compressible than the material of outsole 60, then this configuration may impart lesser compressibility to sole structure 30, particularly the periphery of sole structure 30. Referring to FIG. 15B, projections 64 extend through a majority of the thickness of chamber 50. If the material of plate 40 is less compressible than the material of outsole 60, then this configuration may impart greater compressibility to sole structure 30. In some configurations, projections 44 and 64 may have different relative lengths in different areas of sole structure 30. As an example, FIG. 15C depicts projections 44 as having greater length adjacent to medial side 15 than lateral side 14, may also limit the degree to which the foot pronates during running. Referring to FIG. 15D, the relative slopes of projections 44 and projections 64 are different, which may have an effect upon the relative compressibilities of plate 40 and outsole 60.

Figure 15E:
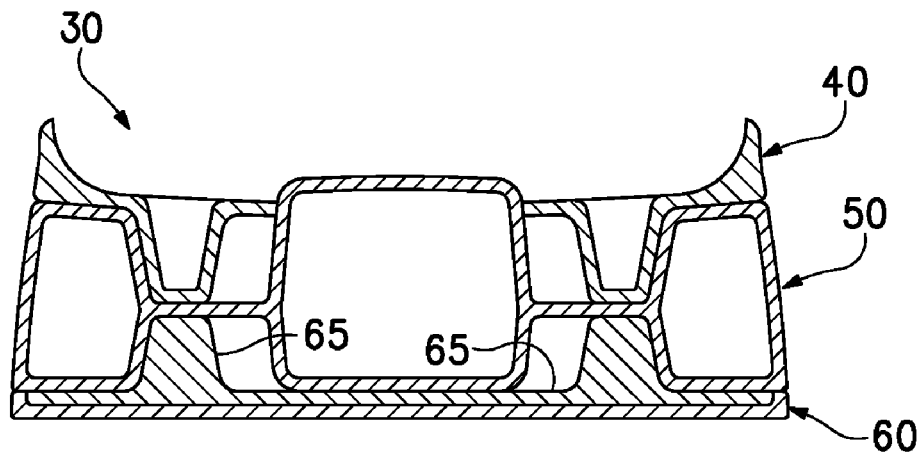
Figure 15F:
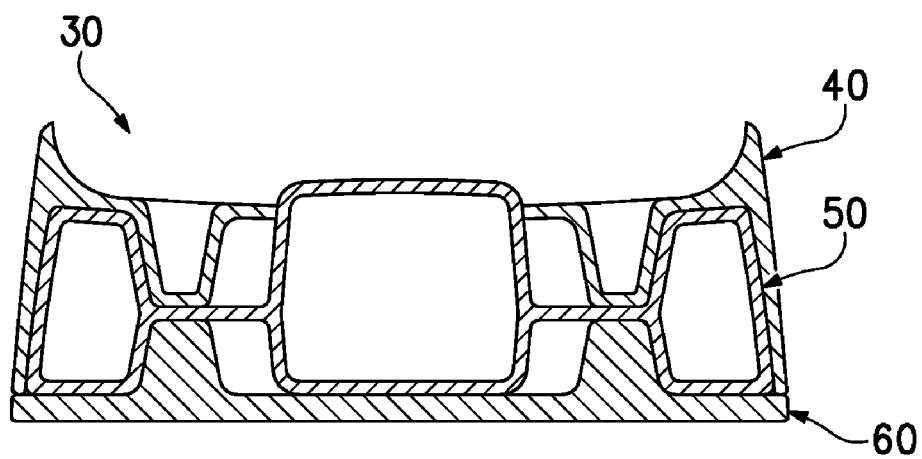

Various other aspects of sole structure 30 may also be modified. In another configuration, a plate 65 rather than outsole 60 may form projections that extend into bonded areas 54 formed by lower surface 52 of chamber 50, as depicted in FIG. 15E. Referring to FIG. 15F, side portions of plate 40 extend downward and extend along sidewall surface 53, thereby covering the sides of chamber 50. Side portions of plate 40 may also extend upward and have a configuration that interfaces with the sides of upper 20, thereby forming a heel counter, for example, that resists sideways or rearward movement of the foot. In further configurations, other portions of plate 40 may extend upward to form an arch support or a toe cap that protects forward portions of upper 20.

Figure 16A:
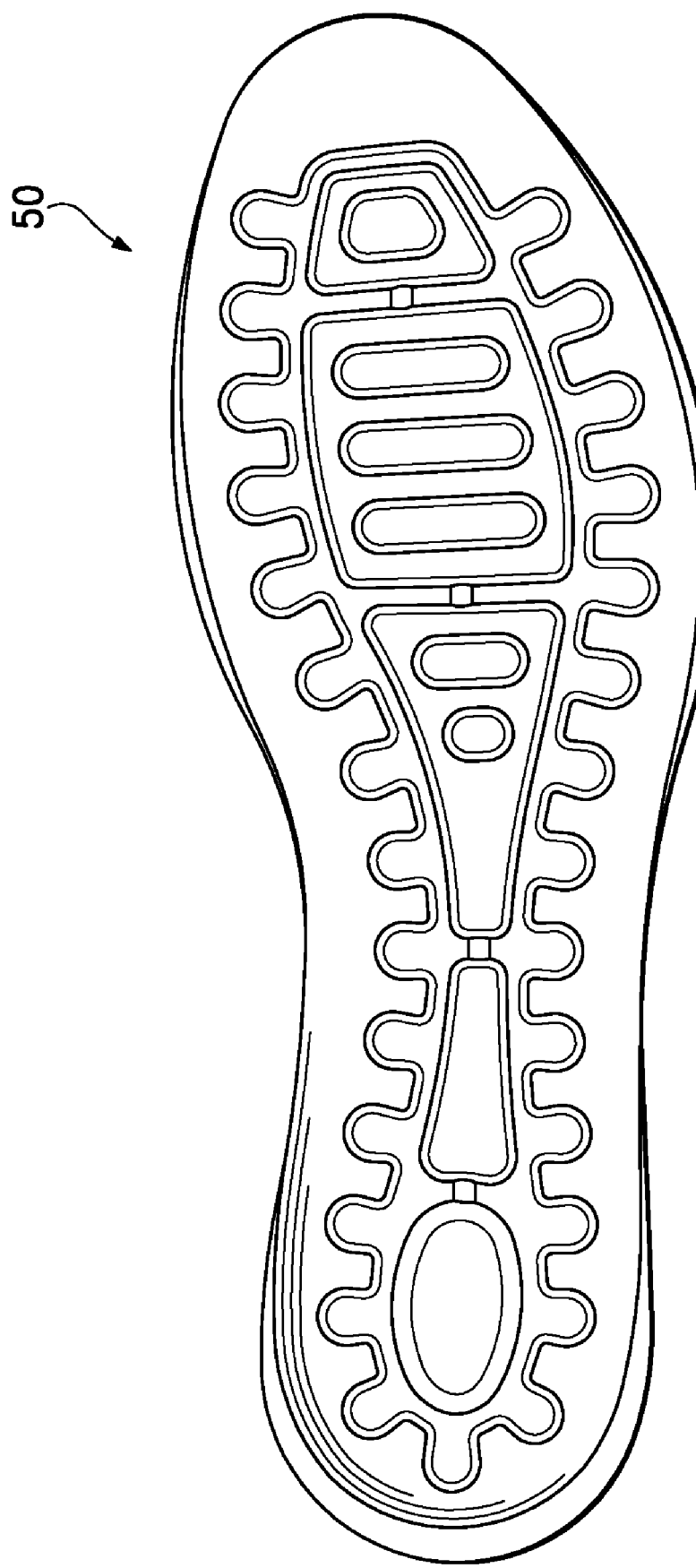
FIGS. 16A-16C are top plan views corresponding with FIG. 11 and depicting further configurations of the chamber of the first sole structure.
Figure 16B:
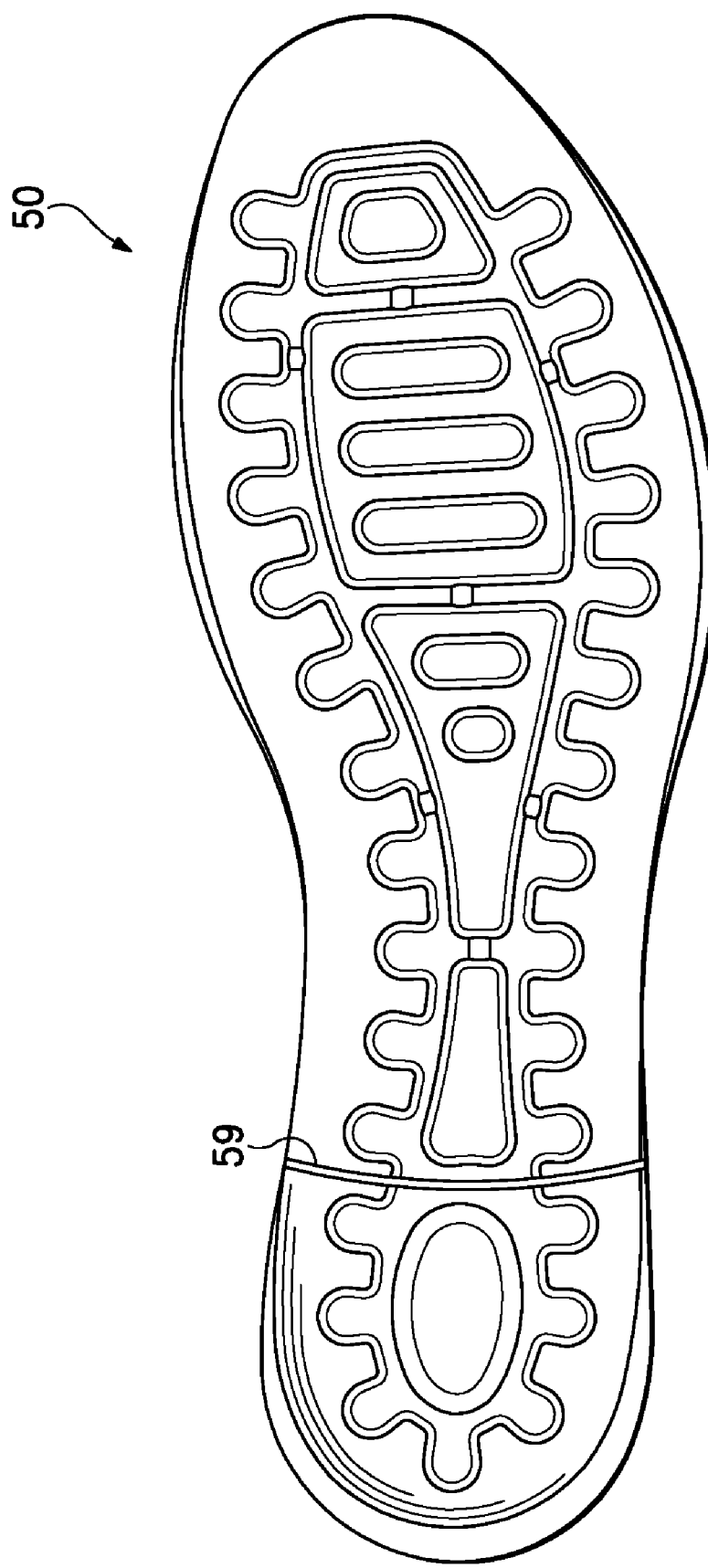
Figure 16C:
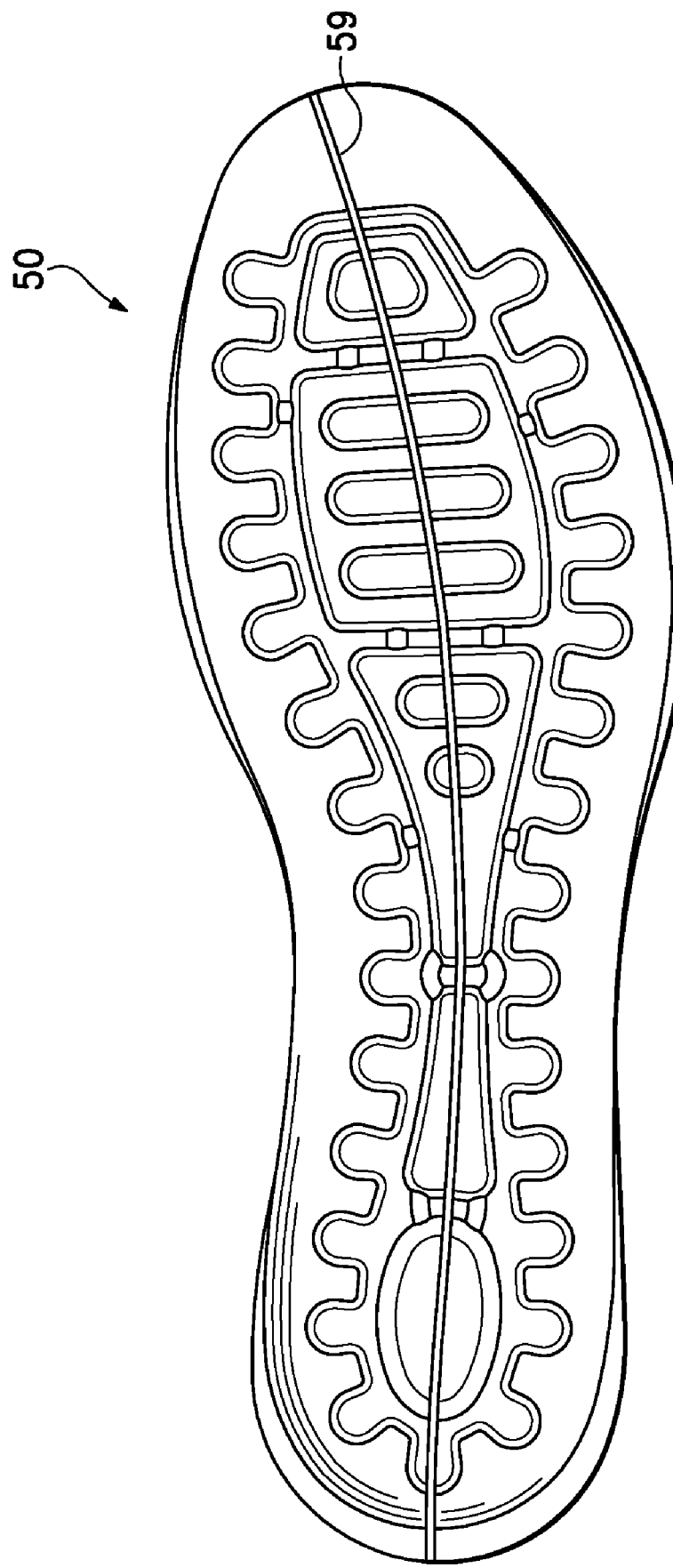
Figure 17:
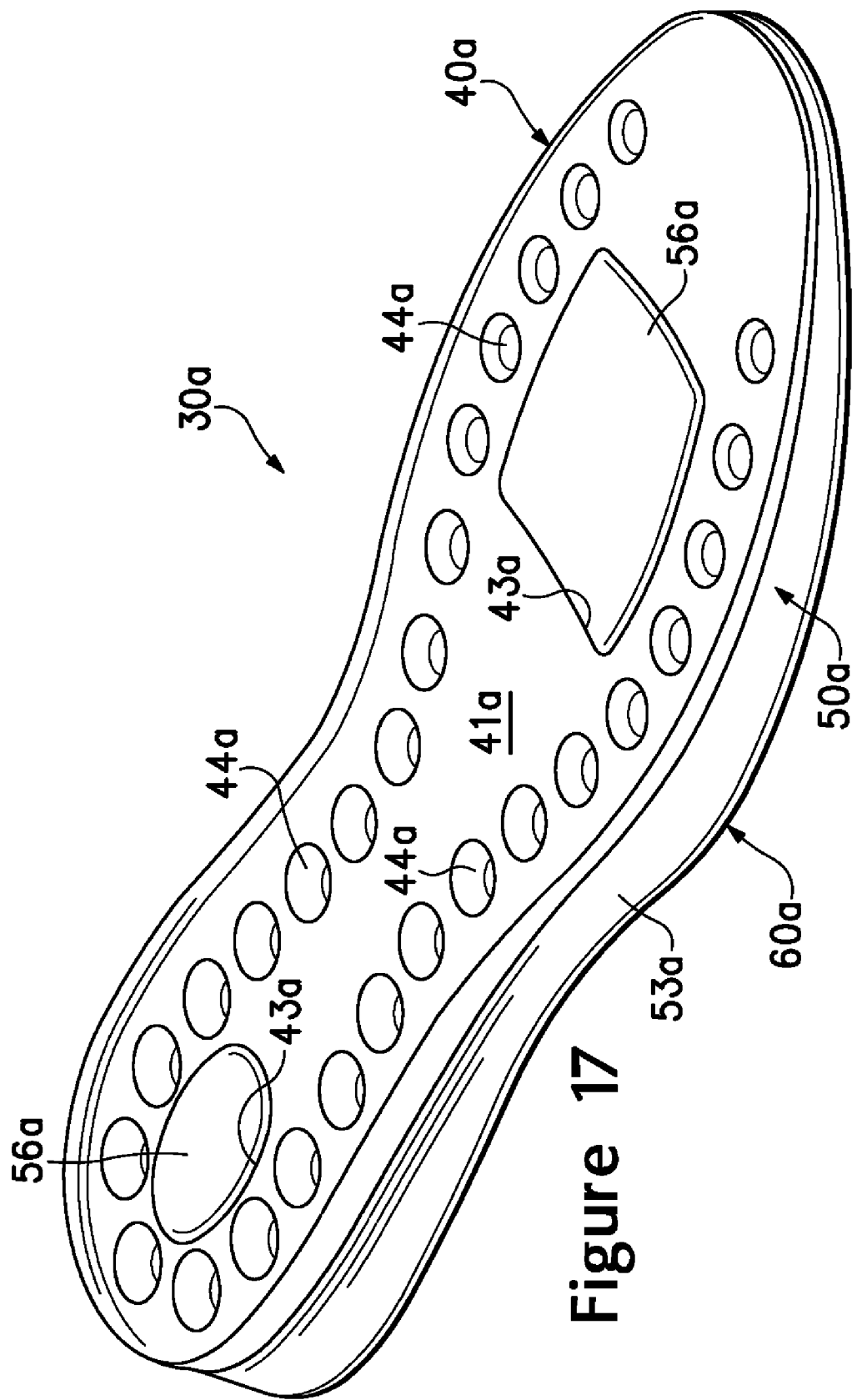
FIG. 17 is a perspective view of a second sole structure of the article of footwear.
Figure 18:
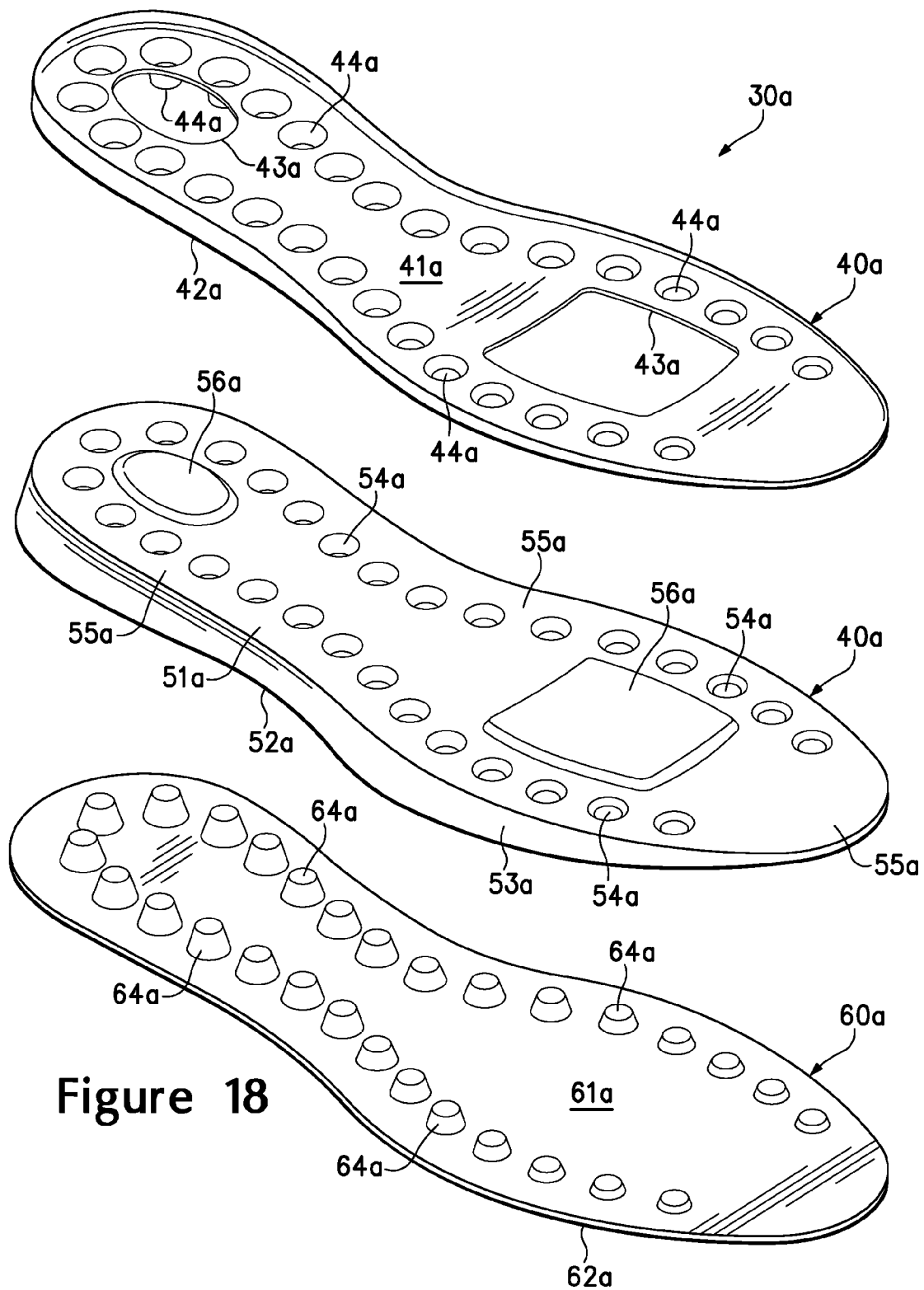
FIG. 18 is an exploded perspective view of the second sole structure.
Figure 19:
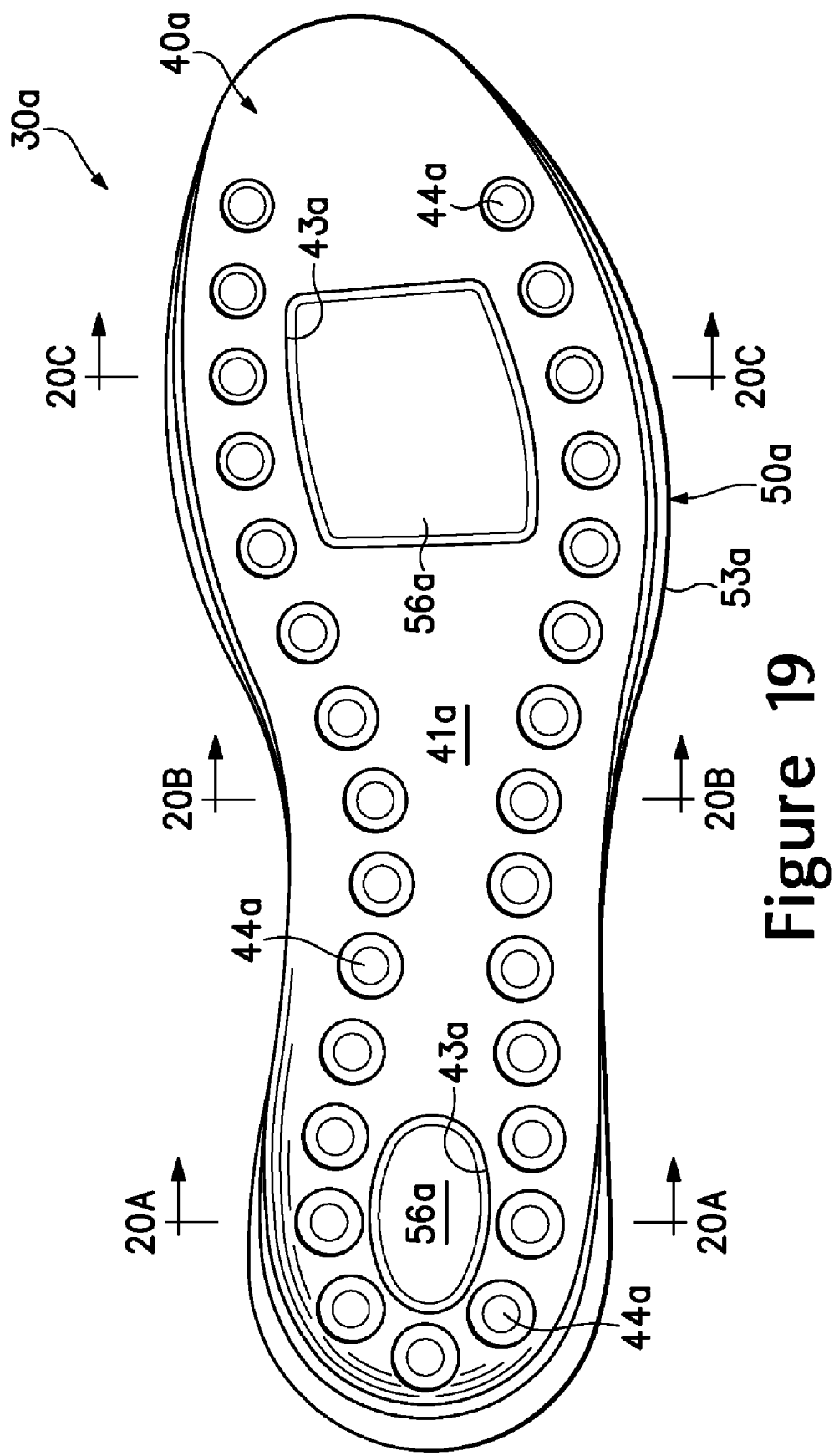
FIG. 19 is a top plan view of the second sole structure.
Figure 20A:
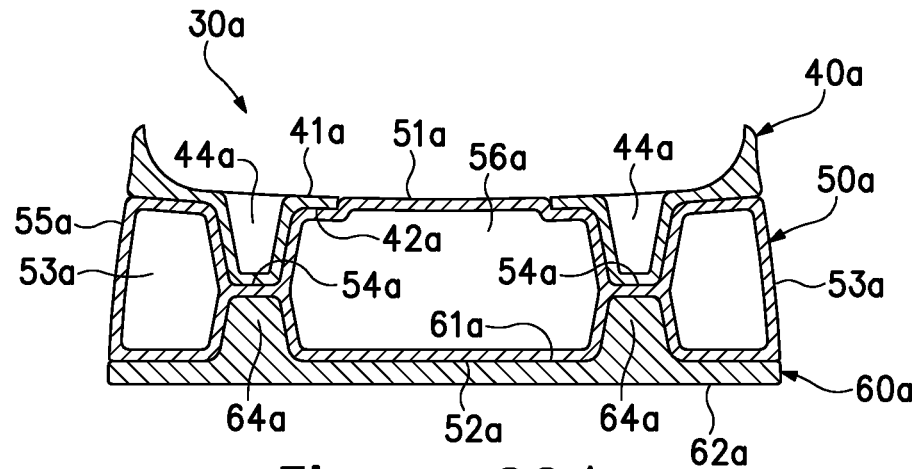
FIGS. 20A-20C are cross-sectional views of the second sole structure, as defined by section lines 20A-20C in FIG. 19.
Figure 20B:
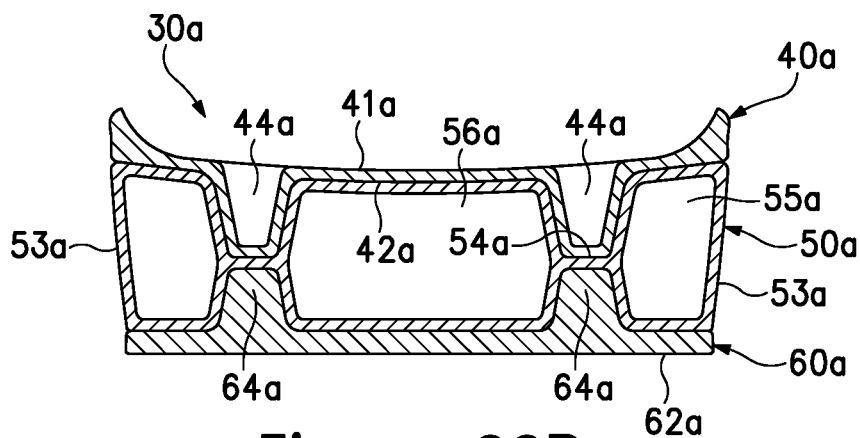
Figure 20C:
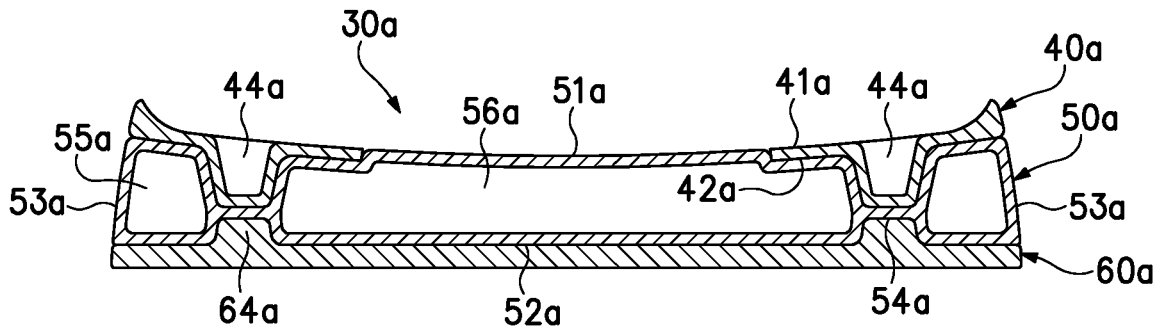
Figure 21:
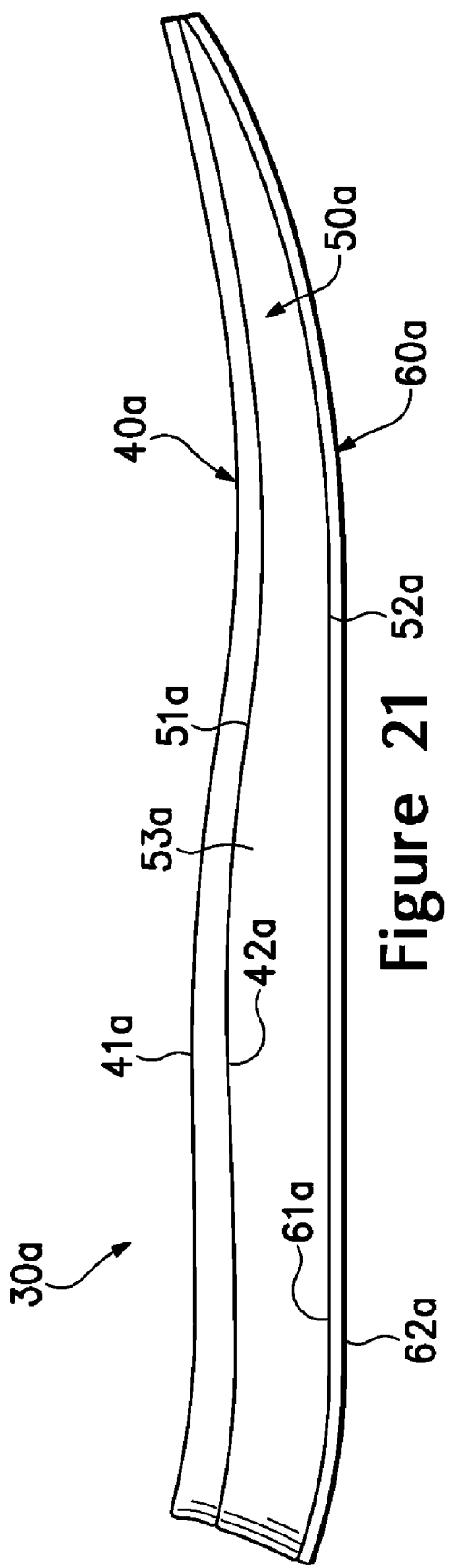
FIG. 21 is a lateral side elevational view of the second sole structure.
Figure 22:
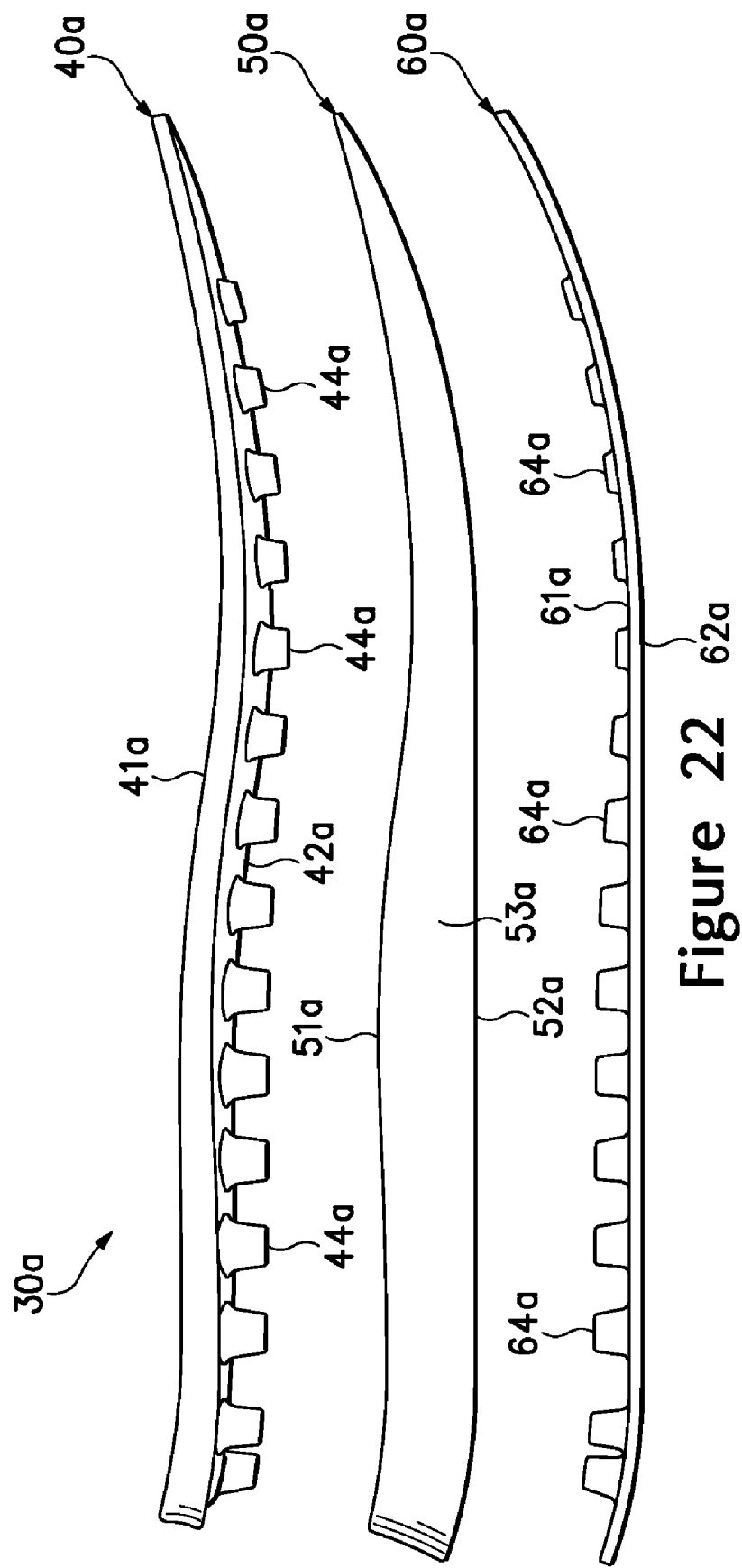
FIG. 22 is an exploded lateral side elevational view of the second sole structure.

Modifications may also be made to chamber 50 in order to vary the resulting properties of sole structure 30. Referring to FIG. 16A, conduits 57 are sealed or otherwise absent from chamber 50, thereby preventing fluid communication between subchambers 55 and 56. This configuration may permit subchambers 55 and 56 to be inflated to different pressures. In some configurations, portions of chamber 50 may also be segregated to form different zones of pressure, as depicted in FIG. 16B, in which a bond 59 segregates the fluid within heel region 13 from the fluid within forefoot region 11 and midfoot region 12. In other configurations, a longitudinal bond 59 may form separate chambers adjacent to lateral side 14 and medial side 15, as depicted in FIG. 16C. When inflated to different pressures, the separate chambers may limit the degree to which the foot pronates during running.

Second Sole Structure Configuration

In addition to sole structure 30, sole structure 30a may be utilized with upper 20 to form footwear 10. The primary elements of sole structure 30a are a plate 40a, a chamber 50a, and an outsole 60a, as depicted in FIGS. 17-22. Plate 40a forms an upper portion of sole structure 30a and is positioned adjacent to upper 20. Chamber 50a forms a middle portion of sole structure 30a and is positioned between plate 40a and outsole 60a. In addition, outsole 60a forms a lower portion of sole structure 30a and is positioned to engage the ground. Each of plate 40a, chamber 50a, and outsole 60a extend around a perimeter of sole structure 30a and have a shape that generally corresponds with an outline of the foot. Accordingly, each of plate 40a, chamber 50a, and outsole 60a are exposed to an exterior of footwear 10 and cooperatively form a side surface of sole structure 30a. In further configurations, however, upper 20 may extend over the sides of plate 40a, edges of plate 40a may be spaced inward from the side surface of sole structure 30a, or portions of plate 40a and outsole 60a may cover the sides of chamber 50a, for example.

Plate 40a exhibits the general configuration of plate 40 and has an upper surface 41a and an opposite lower surface 42a. Two apertures 43a extend between surfaces 41a and 42a to form openings that expose portions of chamber 50a. Whereas upper surface 41a has a generally smooth aspect that is contoured to conform with the general anatomical structure of the foot, lower surface 42*a* defines a plurality of downwardly-extending projections 44*a* that extend into depressions in chamber 50*a*. Plate 40*a* may be manufactured from any of the diverse materials discussed above for plate 40.

Chamber 50*a* has a configuration that is similar to chamber 50 and is formed from a polymer material that provides a sealed barrier for enclosing a fluid. The polymer material defines an upper surface 51*a*, an opposite lower surface 52*a*, and a sidewall surface 53*a* that extends around a periphery of chamber 50*a* and between surfaces 51*a* and 52*a*. Chamber 50*a* includes various bonded areas 54*a* where upper surface 51*a* is bonded or otherwise joined to lower surface 52*a*. In contrast with bonded areas 54 of chamber 50, bonded areas 54*a* are limited to the locations that receive projections 44*a* and the corresponding projections from outsole 50*a*. Chamber 50*a* may be manufactured from any of the diverse materials discussed above for chamber 50. In addition, the various fluids and the range of fluid pressures discussed above for chamber 50 may also be used for chamber 50*a*.

Outsole 60*a* has a configuration that is similar to outsole 60 and forms the ground-contacting portion of sole structure 30*a*. Outsole 60*a* has an upper surface 61*a* and an opposite lower surface 62*a*. Upper surface 61*a* defines a plurality of upwardly-extending projections 64*a* that extend into bonded areas 54*a* in lower surface 52*a* of chamber 50*a*. Although a variety of materials may be utilized for outsole 60*a*, rubber materials may be utilized to impart durability and wear-resistance. Lower surface 62*a* may also be textured to enhance the traction (i.e., friction) properties between footwear 10 and the ground.

The properties of plate 40*a*, chamber 50*a*, and outsole 60*a* have an effect upon the performance characteristics of footwear 10. That is, the shape and dimensions of plate 40*a*, chamber 50*a*, and outsole 60*a* (e.g., thickness and contour) and the materials that form plate 40*a*, chamber 50*a*, and outsole 60*a* may affect the degree to which sole structure 30*a* attenuates ground reaction forces, imparts stability, and limits foot motions, for example. By varying the shape, dimensions, or materials of plate 40*a*, chamber 50*a*, and outsole 60*a*, therefore, the performance characteristics of footwear 10 may be altered. That is, footwear 10 may be manufactured for different athletic activities by modifying the shape, dimensions, or materials of one or more of plate 40*a*, chamber 50*a*, and outsole 60*a*. Accordingly, any of the variations discussed above for sole structure 30 may also be utilized with sole structure 30*a*.

Manufacturing Methods For The Second Sole Structure

A variety of techniques may be utilized to manufacture sole structure 30*a*. As an example, chamber 50*a* may be formed from a pair of polymer sheets that are molded and bonded during a thermoforming process. More particularly, the thermoforming process (a) imparts shape to one of the polymer sheets in order to form upper surface 51*a*, (b) imparts shape to the other of the polymer sheets in order to form lower surface 52*a*, (c) forms sidewall surface 53*a* from one or both of the sheets, and (d) forms bonded areas 54*a* to join interior portions of surfaces 41*a* and 42*a*. Once chamber 50*a* is formed, each of plate 40*a* and outsole 60*a* are secured to opposite sides of chamber 50*a*, through adhesive bonding or heat bonding, for example. Chamber 50*a* may also be formed from a blowmolding process wherein a parison or molten or uncured polymer material extends between mold portions having a shape of chamber 50*a*. The polymer material is then drawn into the mold to impart the shape of chamber 50*a*. Upon cooling or curing, chamber 50*a* is removed from the mold and each of plate 40*a* and outsole 60*a* are secured to opposite sides of chamber 50*a*.

Figure 23A:
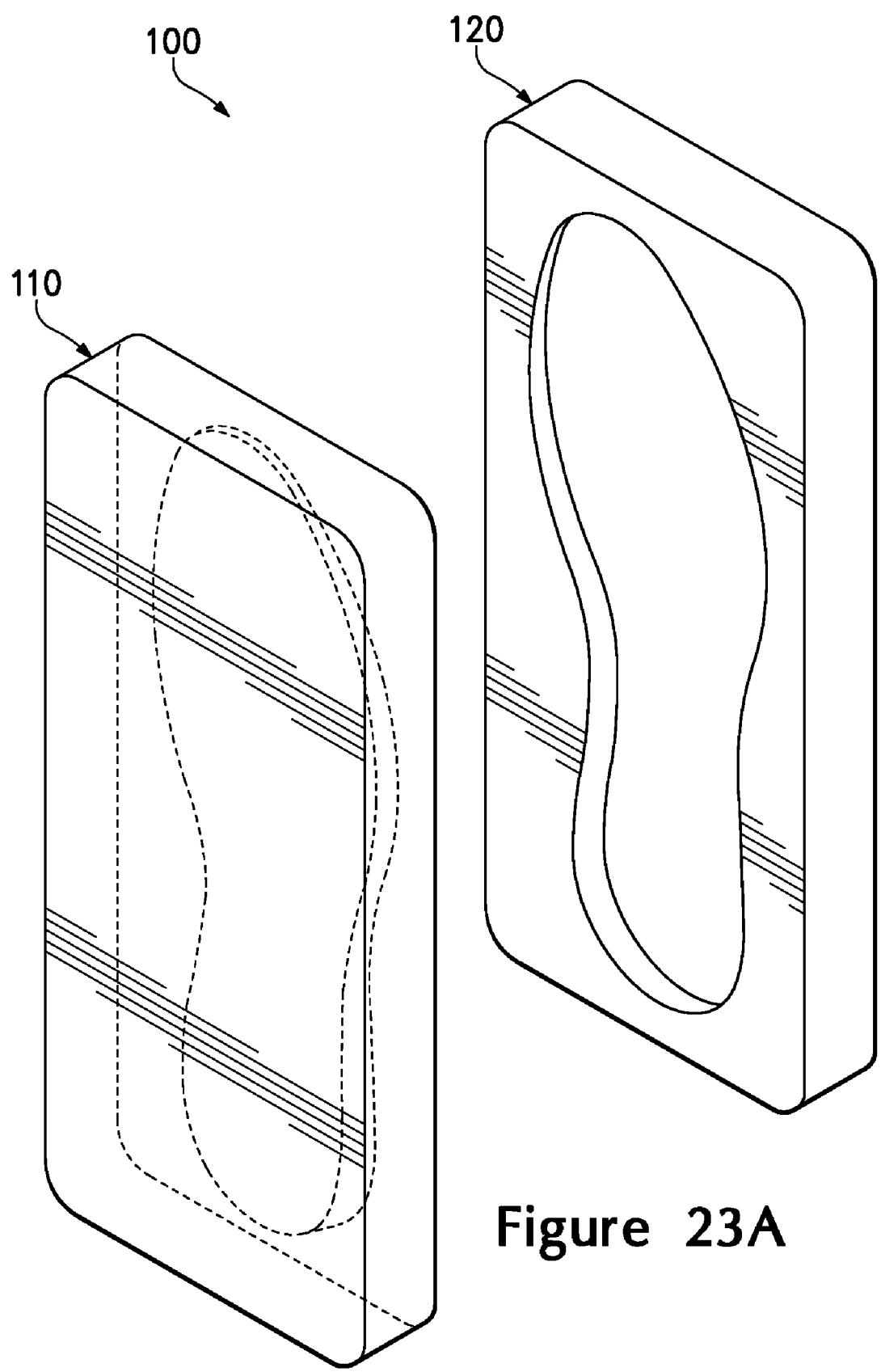
FIGS. 23A-23B are perspective views of a mold for forming the second sole structure.
Figure 23B:
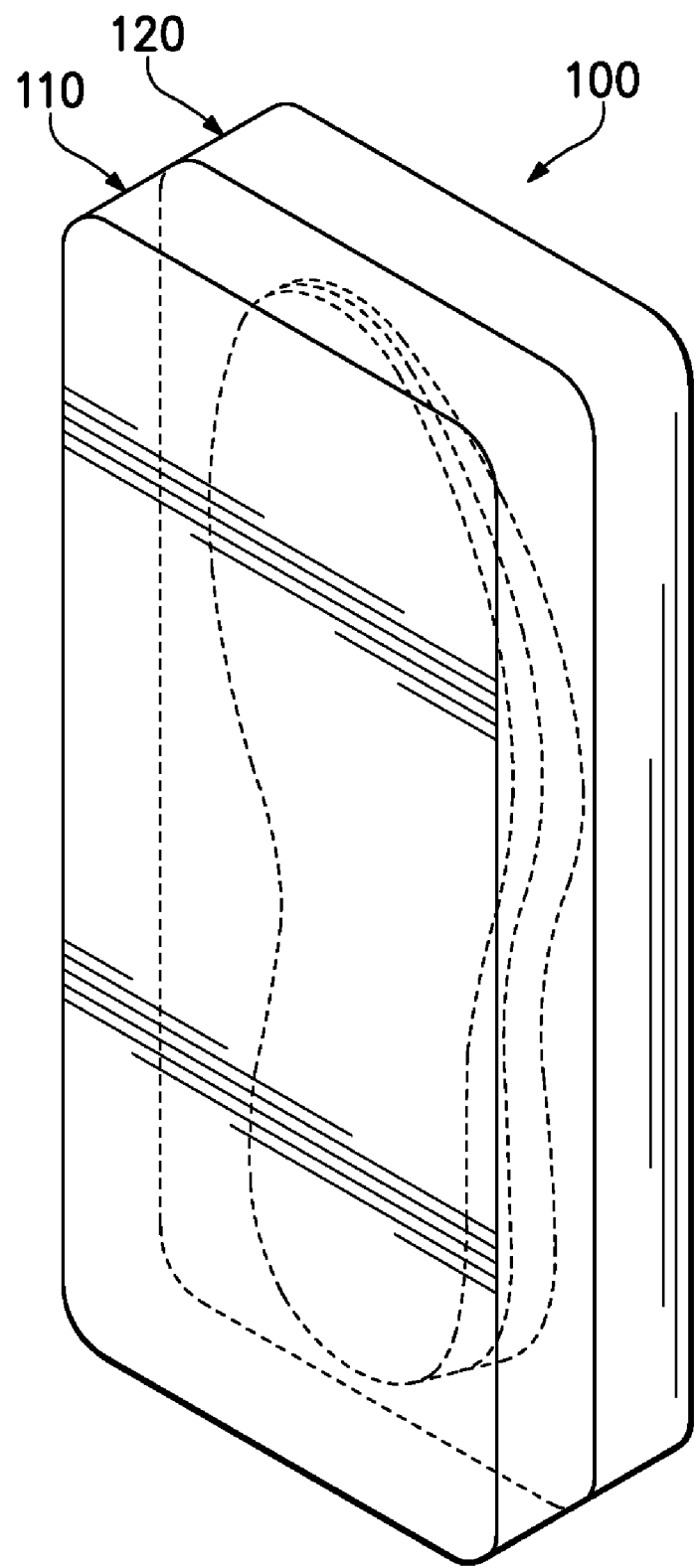

The techniques for manufacturing sole structure 30*a* discussed above generally involve forming each component separately and then joining the components together. As an alternative, chamber 50*a* may be formed and simultaneously joined to each of plate 40*a* and outsole 60*a* utilizing a mold 100, which is depicted in FIG. 23A. Mold 100 includes a first mold portion 110 and a corresponding second mold portion 120. When joined together, as depicted in FIG. 23B, mold portions 110 and 120 form a cavity having dimensions substantially equal to the exterior dimensions of sole structure 30*a* (i.e., the combination of plate 40*a*, chamber 50*a*, and outsole 60*a*). Mold 100 may be utilized for blowmolding chamber 50*a* and simultaneously bonding or otherwise securing plate 40*a* and outsole 60*a* to the exterior of chamber 50*a*. In general, plate 40*a* is placed within first mold portion 110 and outsole 60*a* is placed within second mold portion 120. A parison, which is generally a tube of molten or uncured polymer material, extends between mold portions 110 and 120. The parison is then drawn into mold 100 and against the surfaces of plate 40*a* and chamber 60*a* having projections 44*a* and 64*a*, and the parison is drawn against exposed surfaces of the cavity within mold 100. Once the material in the parison has conformed to the shapes of plate 40*a*, outsole 60*a*, and mold 100, mold portions 110 and 120 separate to permit sole structure 30*a* to be removed. When formed through this method, the surfaces of chamber 50*a* correspond with the contours in lower surface 42*a* of plate 40*a* and also in upper surface 61*a* of outsole 60*a*.

The manner in which mold 100 is utilized to form sole structure 30*a* will now be discussed in greater detail. An injection-molding process, for example, may be utilized to form plate 40*a* and outsole 60*a* from any of the materials discussed above. Plate 40*a* and outsole 60*a* are then cleansed with a detergent or alcohol, for example, in order to remove surface impurities, such as a mold release agent or fingerprints. The surfaces of plate 40*a* and outsole 60*a* may also be plasma treated to enhance bonding with chamber 50*a*.

Figure 24A:
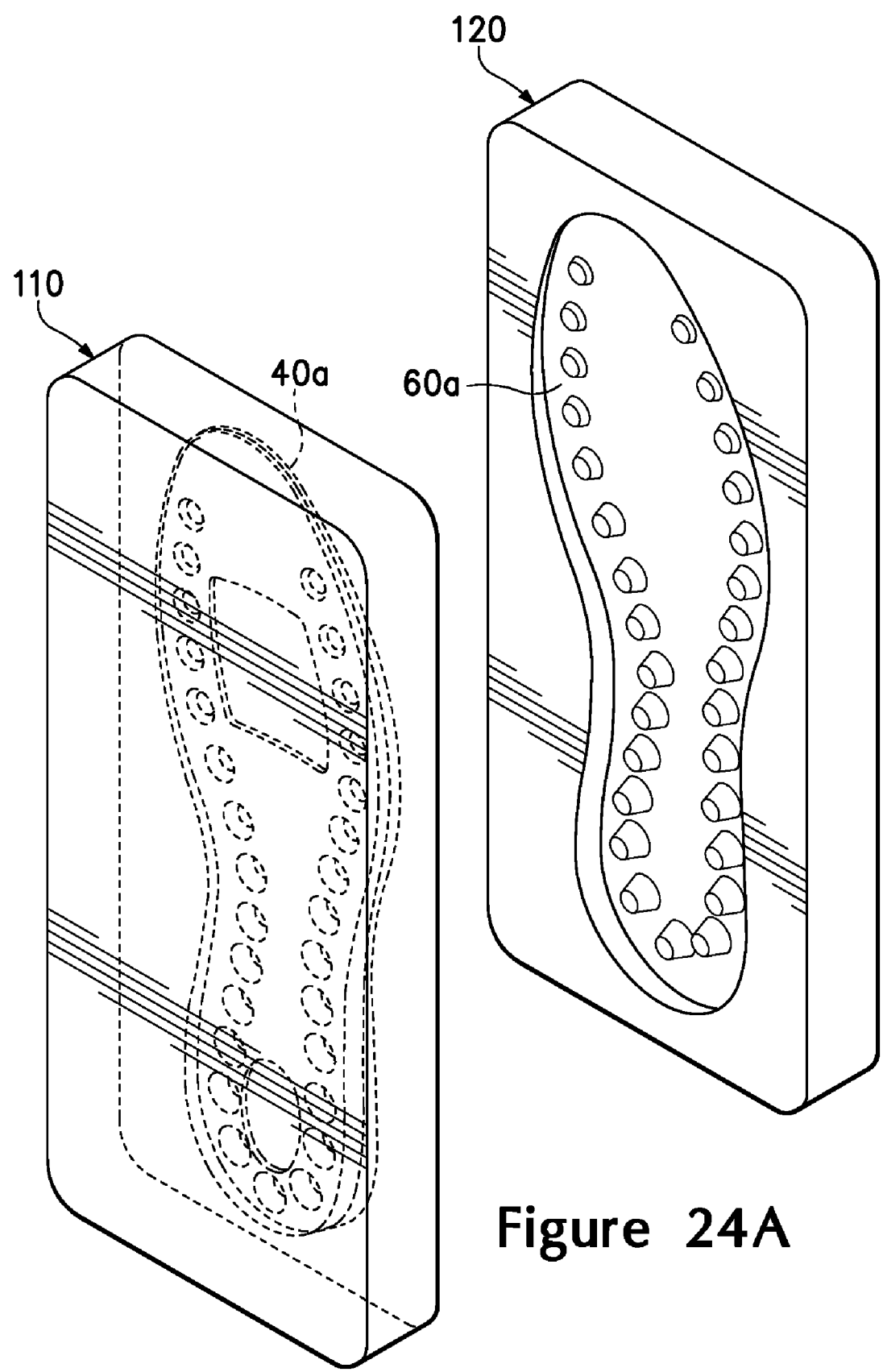
FIGS. 24A-24E are perspective views of a method of manufacturing the second sole structure with the mold.

Following formation and cleansing, plate 40*a* and outsole 60*a* are placed within mold 100. More particularly, plate 40*a* is located within first mold portion 110 and outsole 60*a* is located within second mold portion 120 such that surfaces 42*a* and 61*a* face each other, as depicted in FIG. 24A. A variety of techniques may be utilized to secure plate 40*a* and outsole 60*a* within upper mold portions 110 and 120, including a vacuum system, various seals, or non-permanent adhesive elements, for example. In addition, plate 40*a* and outsole 60*a* may include various tabs that define apertures, and mold portions 110 and 120 may include protrusions that engage the apertures to secure plate 40*a* and outsole 60*a* within mold 100.

A plurality of conduits may extend through mold 100 in order to channel a heated liquid, such as water, through mold 100 to raise the overall temperature of mold 100. When plate 40*a* and outsole 60*a* are positioned within mold 100, plate 40*a* and outsole 60*a* may conduct heat from mold 100, thereby raising the overall temperature of plate 40*a* and outsole 60*a*. In some manufacturing methods, plate 40*a* and outsole 60*a* may be heated prior to placement within mold 100, or heating may net be necessary for plate 40*a* and outsole 60*a*.

Figure 24B:
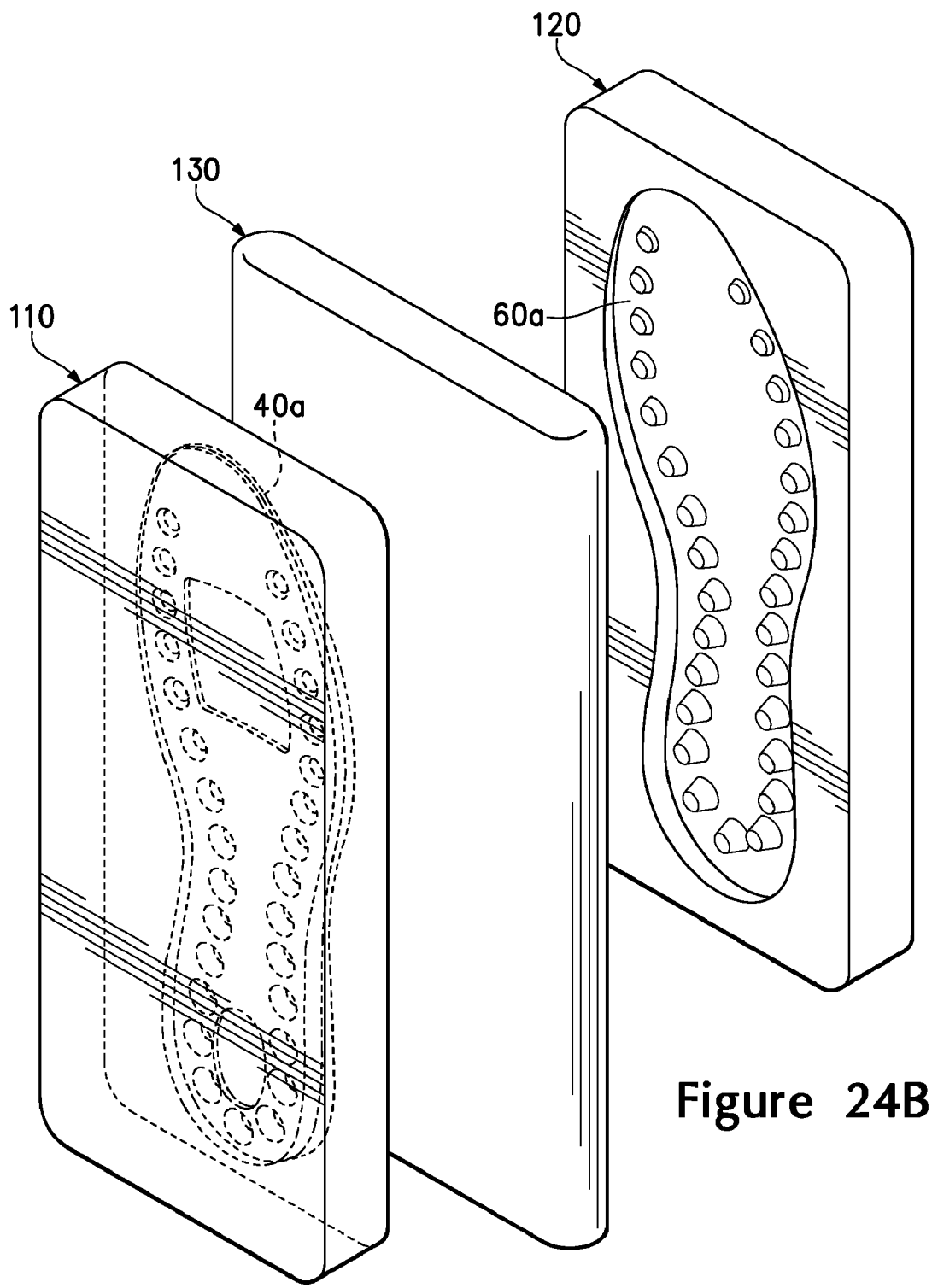
Figure 24C:
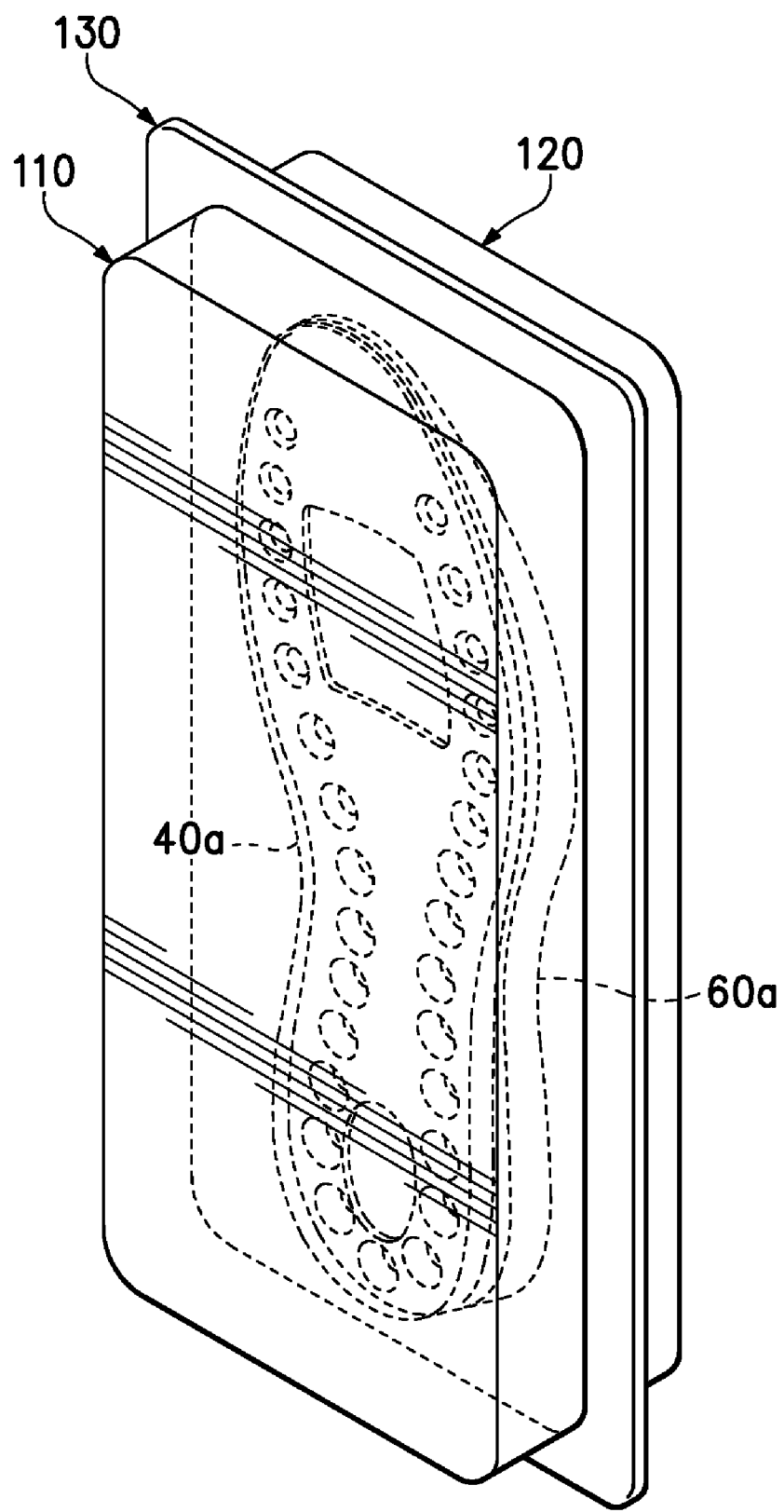

Following placement of plate 40*a* and outsole 60*a* within mold 100, a parison 130 that includes the polymer material for forming chamber 50*a* is positioned between mold portions 110 and 120, as depicted in FIG. 24B. Once parison 130 is properly positioned, mold portions 110 and 120 translate toward each other such that mold 100 contacts and traps a portion of parison 130 within the cavity in mold 100, as depicted in FIG. 24C. As mold portions 110 and 120 translate toward parison 130, a fluid (e.g., air) having a positive pressure in comparison with ambient air may be injected into parison 130 to induce the polymer material of parison 130 to expand and engage the exposed surfaces of plate 40a and outsole 60a (i.e., surfaces 42a and 61a). Expansion of parison 130 also induces the polymer material to engage the exposed surfaces of the cavity within mold 100. Accordingly, the closing of mold 100 coupled with the expansion of parison 130 induces the polymer material to form chamber 50a within the cavity in mold 100 and between the exposed surfaces of plate 40a and outsole 60a.

As parison 130 expands to contact lower surface 42a of plate 40a, upper surface 61a of outsole 60a, and exposed surfaces of the cavity within mold 100, the polymer material of parison 130 stretches, bends, or otherwise conforms to extend around projections 44a and 64a. Portions of parison 130 that are located adjacent the ends of corresponding projections 44a and 64a also contact each other and are bonded to form the various bonded areas 54a. Portions of parison 130 also extend through apertures 43a.

Figure 24D:
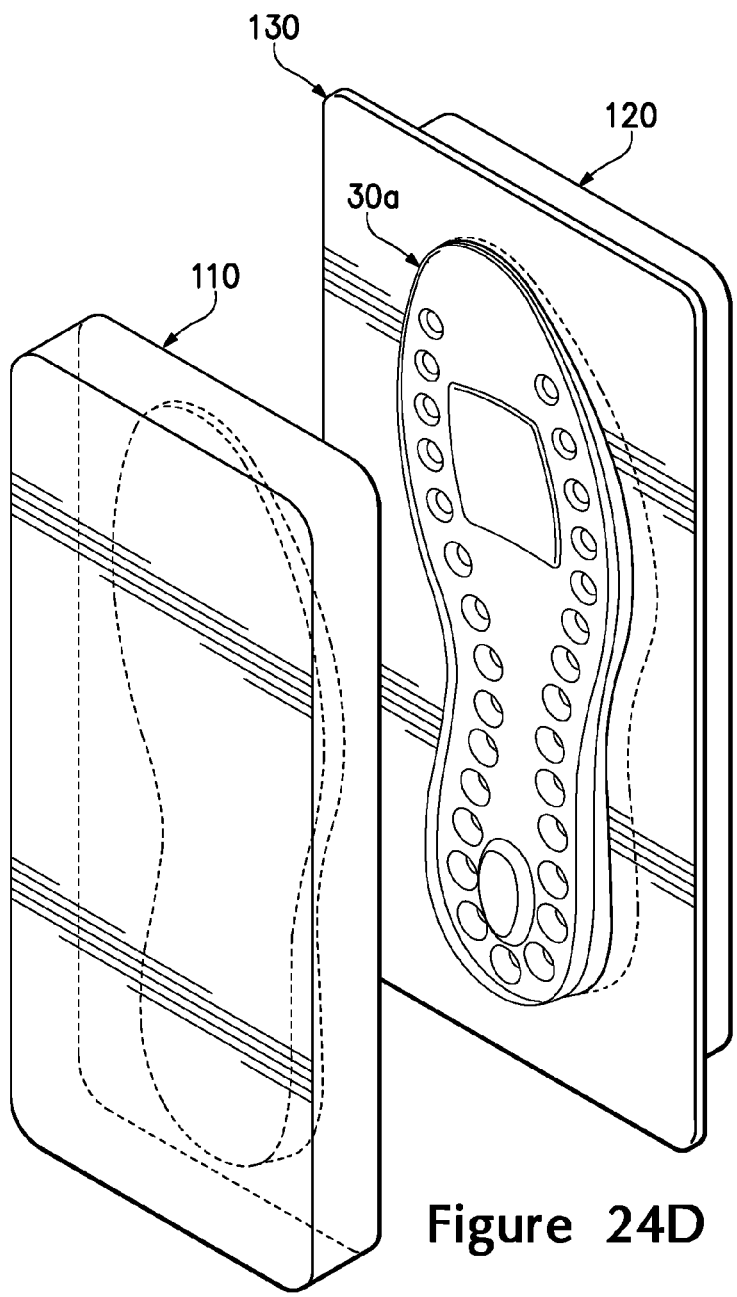
Figure 24E:
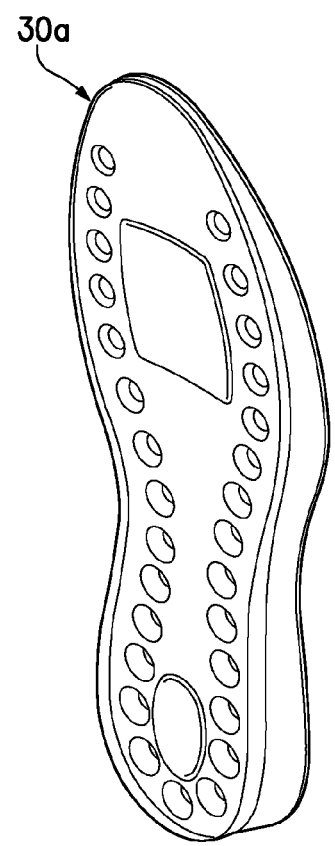
Figure 25:
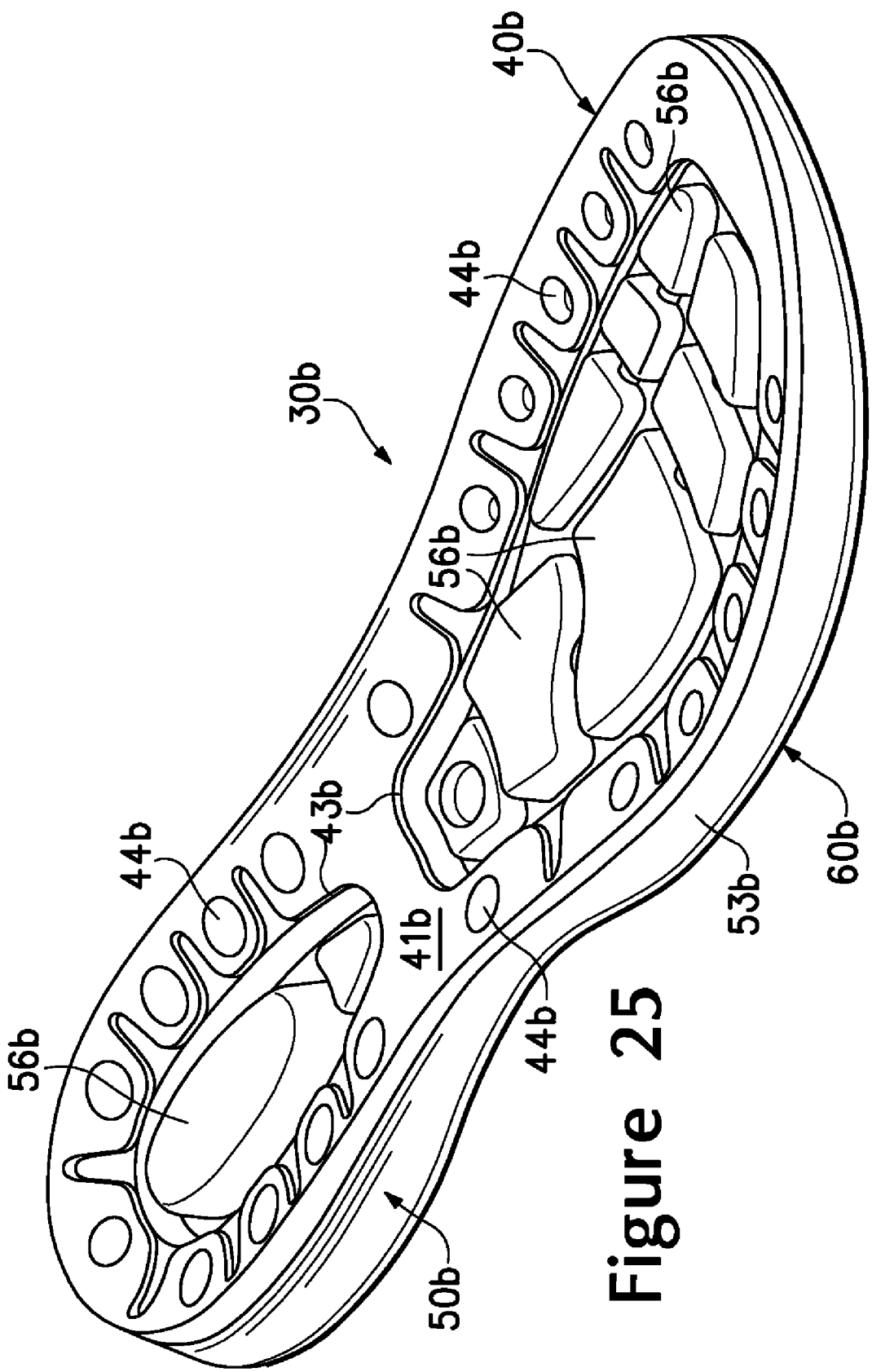
FIG. 25 is a perspective view of a third sole structure of the article of footwear.
Figure 26:
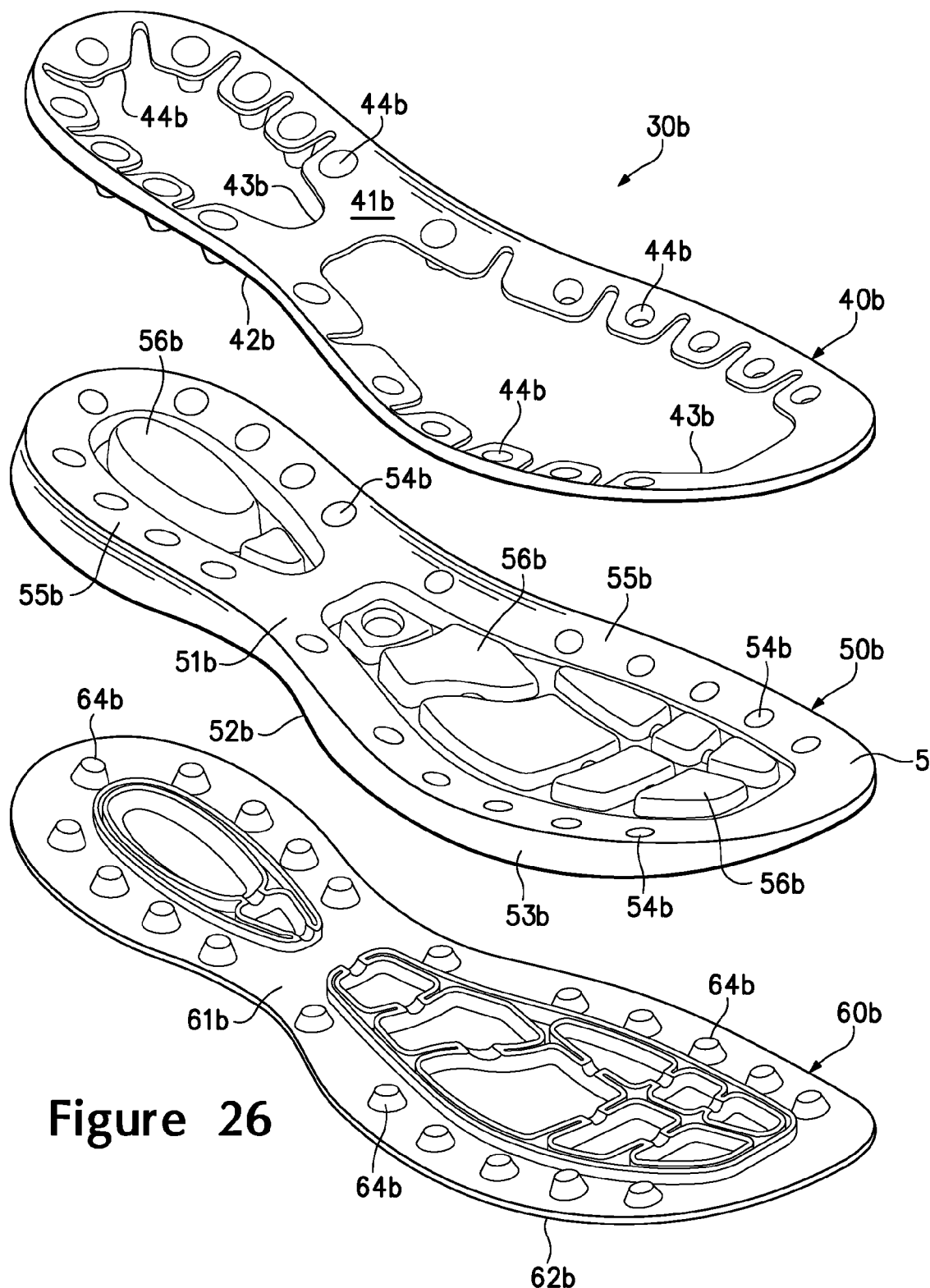
FIG. 26 is an exploded perspective view of the third sole structure.
Figure 27:
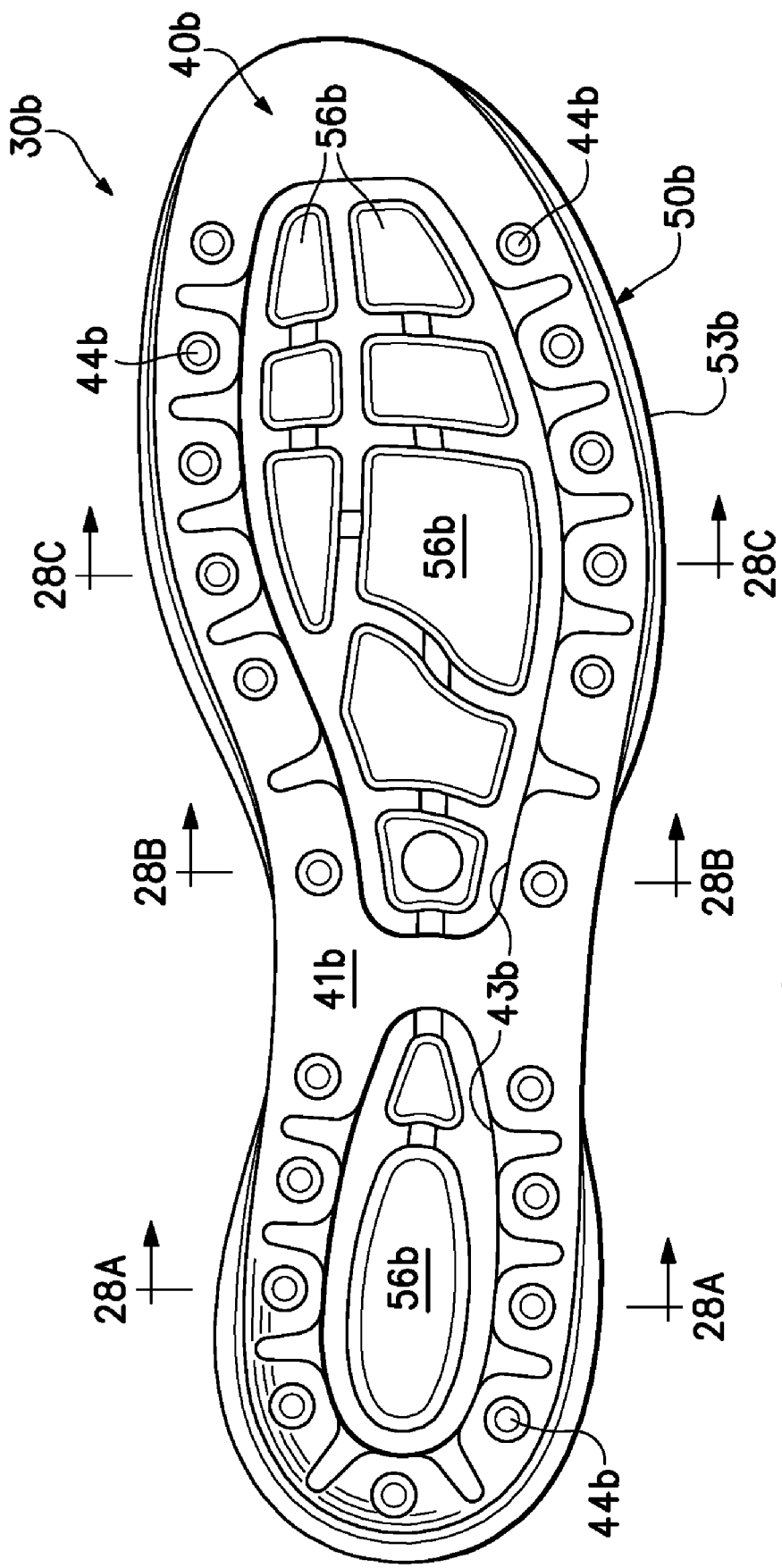
FIG. 27 is a top plan view of the third sole structure.

Once sole structure 30a is formed within mold 100, mold portions 110 and 120 separate such that the combination of plate 40a, chamber 50a, outsole 60a, and excess portions of parison 130 may be removed from mold 100, as depicted in FIG. 24D. The polymer materials forming sole structure 30a are then permitted to cool. If portions of chamber 50a are to be pressurized, then a pressurized fluid may be injected through at this stage of the process. In addition, excess portions of parison 130 may be trimmed or otherwise removed from sole structure 30a at this stage, as depicted in FIG. 24E. The excess portions may then be recycled or reutilized to form additional sole structures. Following the formation of sole structure 30a, upper 20 may be secured to upper surface 41a, thereby substantially completing the manufacture of footwear 10.

Advantages to placing plate 40a and outsole 60a within mold 100 prior to the formation of chamber 50a include manufacturing efficiency and reduced manufacturing expenses. Securing plate 40a and outsole 60a to chamber 50a after the formation of chamber 50a requires the use of an adhesive or a heat bonding operation. In contrast, neither of these are necessary when chamber 50a is formed in mold 100 because the polymer material of parison 130 may bond directly to each of plate 40a and outsole 60a, Accordingly, the number of manufacturing steps may be lessened. When chamber 50a is formed separately, the mold forming chamber 50a is contoured to define bonded areas 54a and other aspects of chamber 50a. In contrast, mold 100 has relatively smooth interior surfaces that are less expensive to manufacture. Accordingly, the expenses associated with forming molds may be decreased.

Although the method of manufacturing sole structure 30a is discussed above as a blowmolding process. Similar concepts may be utilized to form sole structure 30a from a thermoforming process. More particularly, the thermoforming process may involve placing plate 40a and outsole 60a within mold 100 and then locating two sheets of a thermoplastic polymer material between mold portions 110 and 120. As mold portions 110 and 120 translate toward each other, vacuum systems or pressure systems may induce the sheets of thermoplastic polymer material to engage surfaces of plate 40a, outsole 60a, and the cavity within mold 100. In addition, edges of mold portions 110 and 120 may bond the two sheets to each other to seal chamber 50a. Accordingly, the general concept of locating plate 40a and outsole 60a within a mold prior to the formation of chamber 50a may be utilized with a variety of manufacturing processes.

The general manufacturing method discussed above may also be applied to a variety of other sole structure configurations. Although plate 40a and outsole 60a are discussed as having the various projections 44a and 64a, the manufacturing method may be utilized in configurations where projections 44a and 64a are absent. In some configurations, the manufacturing method may be utilized to join sole members of any type (i.e., not a plate or an outsole) to a fluid-filled chamber. That is, moderators, stability devices, textile elements, stiffeners, reinforcing members, and a variety of other footwear elements may be located within a mold and joined to a chamber. Accordingly, a variety of footwear elements may be located within a mold and utilized to at least partially shape polymer elements that form a fluid-filled chamber.

Third Sole Structure Configuration

As an alternative to sole structure 30, sole structure 30b may also be utilized with upper 20 to form footwear 10. The primary elements of sole structure 30b are a plate 40b, a chamber 50b, and an outsole 60b, as depicted in FIGS. 25-30. Plate 40b forms an upper portion of sole structure 30b and is positioned adjacent to upper 20. Chamber 50b forms a middle portion of sole structure 30b and is positioned between plate 40b and outsole 60b. In addition, outsole 60b forms a lower portion of sole structure 30b and is positioned to engage the ground. Each of plate 40b, chamber 50b, and outsole 60b extend around a perimeter of sole structure 30b and have a shape that generally corresponds with an outline of the foot. Accordingly, each of plate 40b, chamber 50b, and outsole 60b are exposed to an exterior of footwear 10 and cooperatively form a side surface of sole structure 30b. In further configurations, however, upper 20 may extend over the sides of plate 40b, edges of plate 40b may be spaced inward from the side surface of sole structure 30b, or portions of plate 40b and outsole 60b may cover the sides of chamber 50b, for example.

Plate 40b exhibits the general configuration of plate 40 and has an upper surface 41b and an opposite lower surface 42b. Two apertures 43b extend between surfaces 41b and 42b to form openings that expose portions of chamber 50b. In comparison with apertures 43 and 43a, apertures 43b exhibit a generally larger configuration that exposes a greater area of chamber 50b Whereas upper surface 41b has a generally smooth aspect that is contoured to conform with the general anatomical structure of the foot, lower surface 42b defines a plurality of downwardly-extending projections 44b that extend into depressions in chamber 50b. Plate 40b may be manufactured from any of the diverse materials discussed above for plate 40.

Chamber 50b has a configuration that is similar to chamber 50 and is formed from a polymer material that provides a sealed barrier for enclosing a fluid. The polymer material defines an upper surface 51b, an opposite lower surface 52b, and a sidewall surface 53b that extends around a periphery of chamber 50b and between surfaces 51b and 52b. Chamber 50b includes various bonded areas 54b where upper surface 51b is bonded or otherwise joined to lower surface 52b. Bonded areas 54b may be configured to form a plurality of separate subchambers within chamber 50b, which may be pressurized to different degrees, or bonded areas 54b may permit fluid to flow between different areas of chamber 50b. Chamber 50b may be manufactured from any of the diverse materials discussed above for chamber 50. In addition, the various fluids and the range of fluid pressure discussed above for chamber 50 may also be used for chamber 50b.

Outsole 60b has a configuration that is similar to outsole 60 and forms the ground-contacting portion of sole structure 30b. Outsole 60b has an upper surface 61b and an opposite lower surface 62b. Upper surface 61b defines a plurality of upwardly-extending projections 64b that extend into bonded areas 54b in lower surface 52b of chamber 50b. Although a variety of materials may be utilized for outsole 60b, rubber materials may be utilized to impart durability and wear-resistance. Lower surface 62b may also be textured to enhance the traction (i.e., friction) properties between footwear 10 and the ground.

Figure 28A:
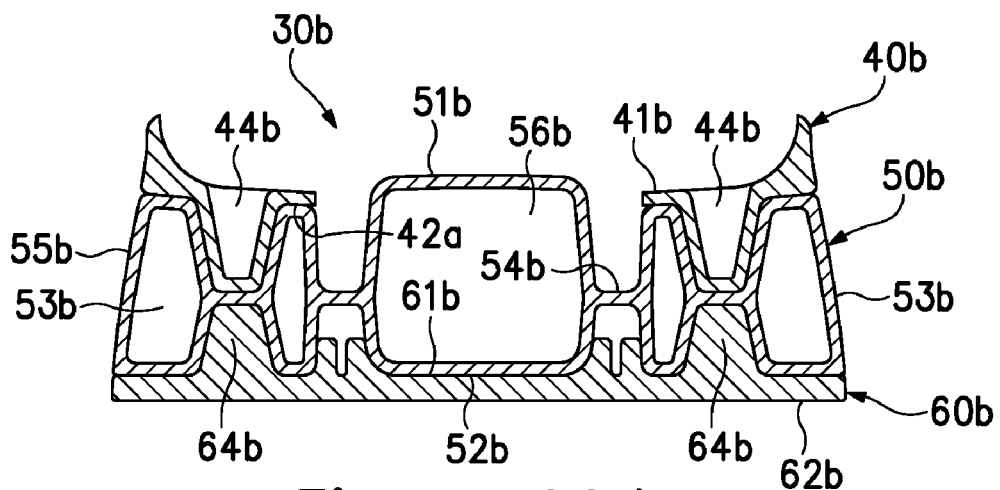
FIGS. 28A-28C are cross-sectional views of the third sole structure, as defined by section lines 28A-28C in FIG. 27.
Figure 28B:
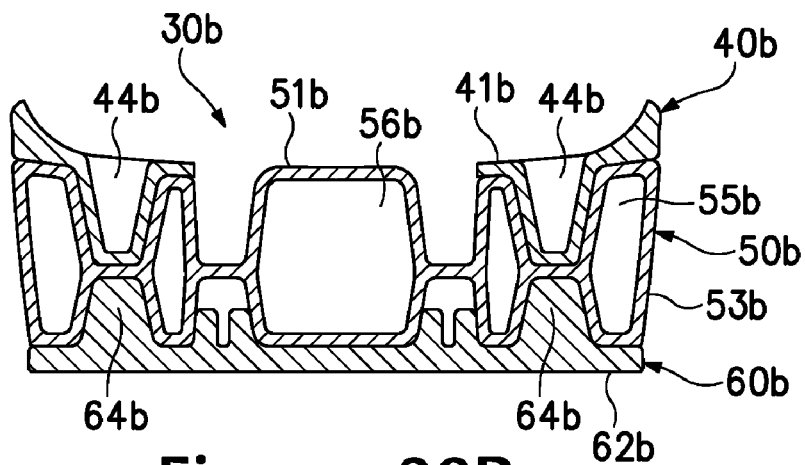
Figure 28C:
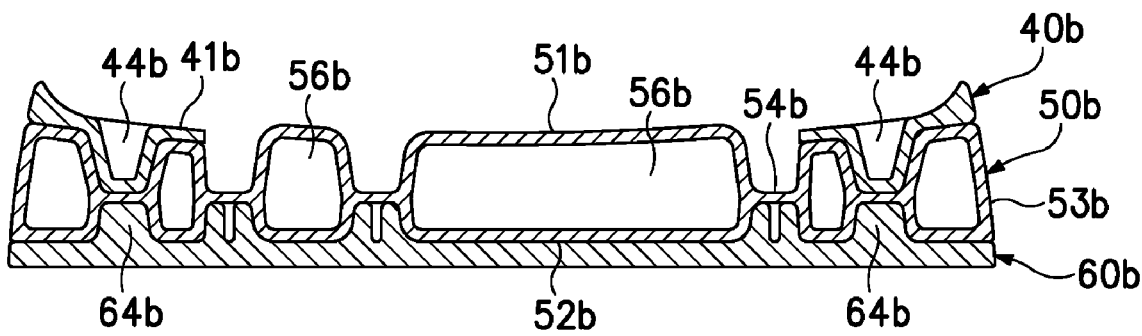
Figure 29:
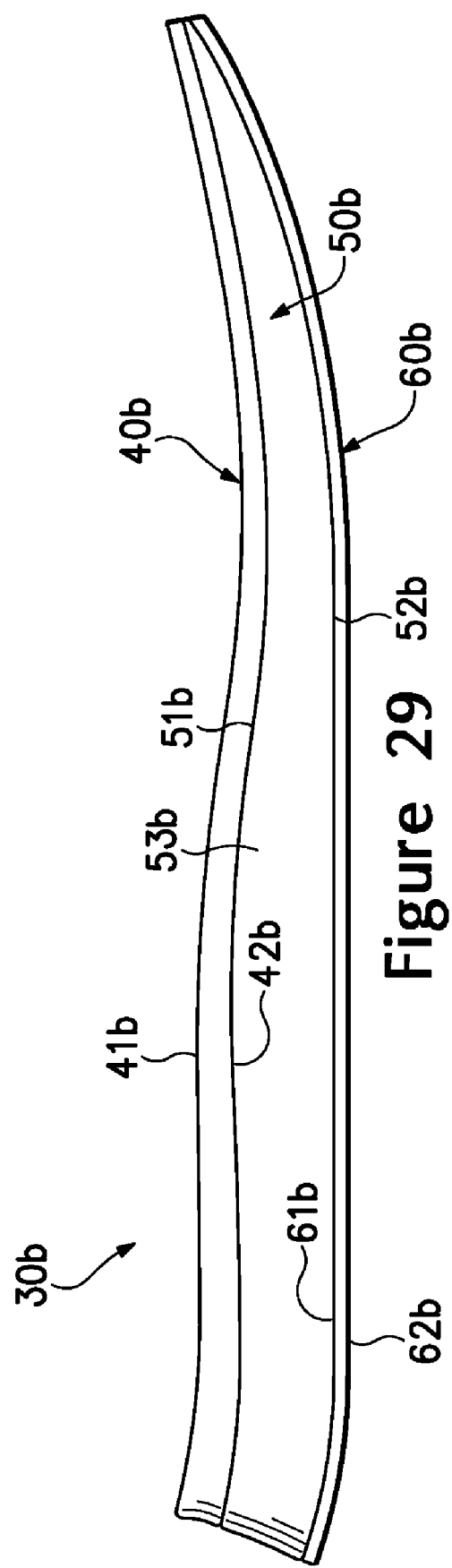
FIG. 29 is a lateral side elevational view of the third sole structure.
Figure 30:
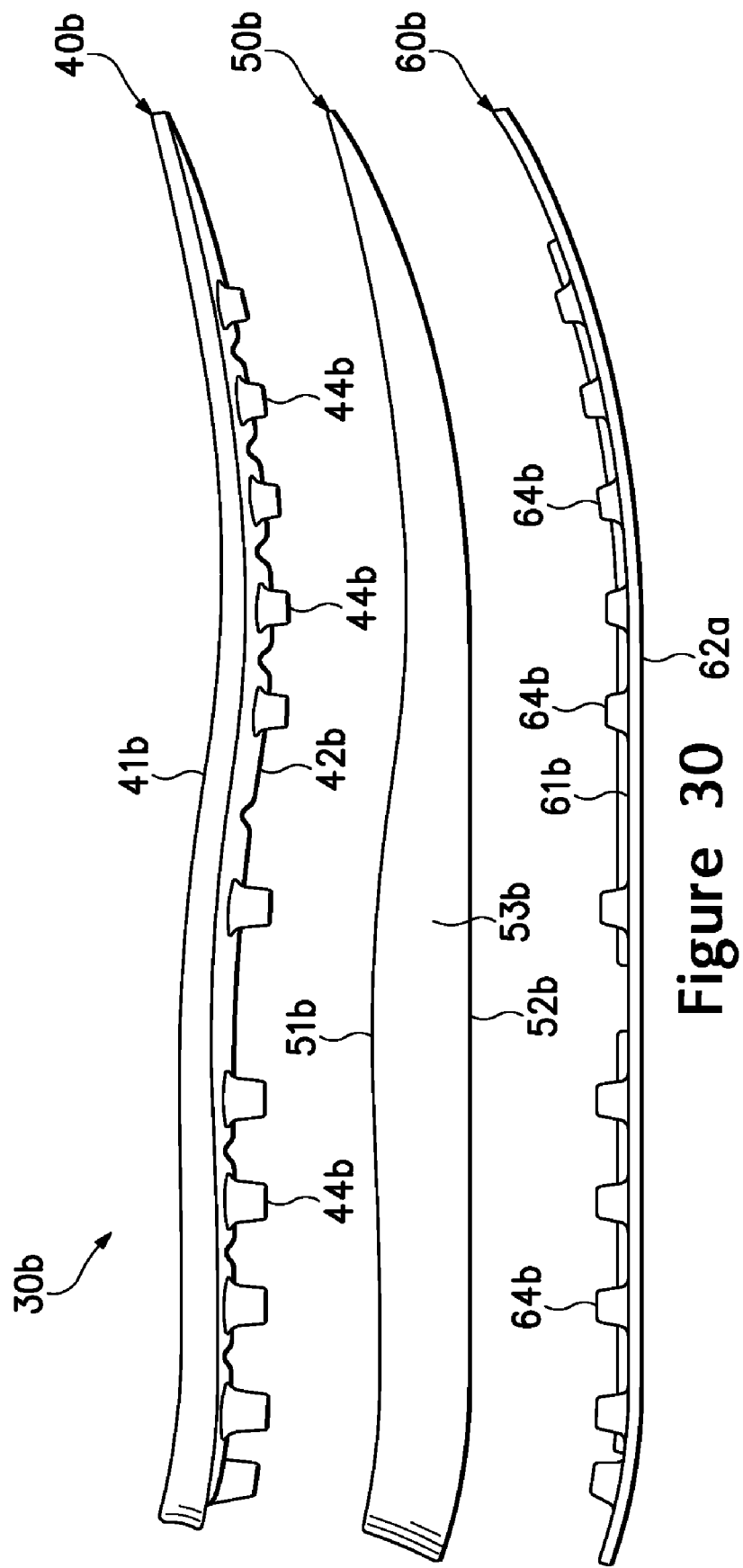
FIG. 30 is an exploded lateral side elevational view of the third sole structure.

Referring to FIGS. 28A-28C, the relative slopes of projections 44b and projections 64b are depicted as being different, which may have an effect upon the relative compressibilities of plate 40b and outsole 60b. Whereas projections 44b taper to a relatively small degree, projections 64b taper to a larger degree. That is, the slopes of each of projections 44b and projections 64b are different.

The properties of plate 40b, chamber 50b, and outsole 60b have an effect upon the performance characteristics of footwear 10. That is, the shape and dimensions of plate 40b, chamber 50b, and outsole 60b (e.g., thickness and contour) and the materials that form plate 40b, chamber 50b, and outsole 60b may affect the degree to which sole structure 30b attenuates ground reaction forces, imparts stability, and limits foot motions, for example. By varying the shape, dimensions, or materials of plate 40b, chamber 50b, and outsole 60b, therefore, the performance characteristics of footwear 10 may be altered. That is, footwear 10 may be manufactured for different athletic activities by modifying the shape, dimensions, or materials of one or more of plate 40b, chamber 50b, and outsole 60b. Accordingly, any of the variations discussed above for sole structure 30 may also be utilized with sole structure 30b. Additionally, any of the manufacturing methods discussed above for sole structure 30 and sole structure 30a may be utilized with sole structure 30b.

The invention is disclosed above and in the accompanying drawings with reference to a variety of embodiments. The purpose served by the disclosure, however, is to provide an example of the various features and concepts related to the invention, not to limit the scope of the invention. One skilled in the relevant art will recognize that numerous variations and modifications may be made to the embodiments described above without departing from the scope of the present invention, as defined by the appended claims.

The invention claimed is:

1. A method of manufacturing an article of footwear, the method comprising:
    inserting a first sole element and a second sole element into a mold, at least one of the first sole element and the second sole element being an outsole of the article of footwear;
    locating a polymer material between the first sole element and the second sole element;
    shaping the polymer material against surfaces of the first sole element, the second sole element, and the mold to form substantially all of a fluid-filled chamber from the polymer material; and
    incorporating the first sole element, the second sole element, and the chamber into the footwear as a sole structure of the footwear.

2. The method recited in claim 1, wherein the step of inserting includes locating the first sole element within a first portion of the mold and locating the second sole element within a second portion of the mold.

3. The method recited in claim 1, wherein the step of locating includes selecting the polymer material to be a parison.

4. The method recited in claim 1, wherein the step of shaping includes bonding the polymer material to each of the first sole element and the second sole element.

5. The method recited in claim 1, further including a step of forming at least one of the first sole element and the second sole element to include projections.

6. The method recited in claim 5, wherein the step of shaping includes forming the polymer material to extend around the projections.

7. The method recited in claim 1, further including a step of forming the first sole element to define an aperture.

8. The method recited in claim 7, wherein the step of shaping includes forming the polymer material to extend into the aperture.

9. The method recited in claim 1, wherein the step of shaping includes sealing air at a substantially ambient pressure within the chamber.

10. A method of manufacturing a sole structure for an article of footwear, the method comprising steps of:
    providing a mold with a first mold portion and a second mold portion that cooperatively define a cavity with a shape of the sole structure;
    inserting a first sole element into a portion of the cavity formed by the first mold portion, the first sole element having an upper surface, an opposite lower surface, and an aperture extending between the upper surface and the lower surface;
    inserting a second sole element into a portion of the cavity formed by the second mold portion, the second sole element having a configuration of an outsole;
    locating a polymer material between the first mold portion and the second mold portion; and
    shaping the polymer material against surfaces of the first sole element, the second sole element, and the cavity to form a fluid-filled chamber from the polymer material and to bond the first sole element and the second sole element to the chamber, a portion of the chamber extending into the aperture.

11. The method recited in claim 10, wherein the step of locating includes selecting the polymer material to be a parison.

12. The method recited in claim 10, wherein the step of shaping includes bonding the polymer material to each of the first sole element and the second sole element.

13. The method recited in claim 10, further including steps of:
    selecting the first sole element to include a plurality of projections; and
    selecting the second sole element to include a plurality of projections.

14. The method recited in claim 13, wherein the step of shaping includes forming the polymer material to extend around the projections.

15. The method recited in claim 13, further including a step of shaping includes sealing air at a substantially ambient pressure within the chamber.

16. A method of manufacturing a sole structure for an article of footwear, the method comprising steps of:
    inserting a plate and an outsole into a cavity of a mold, the plate having a plurality of first projections and the outsole having a plurality of second projections, the first projections extending outward from the plate and toward the second projections, and the second projections extending outward from the outsole and toward the first projections;
    locating a polymer material within the cavity and between the plate and the outsole;
    translating the plate and the outsole toward each other; and
    shaping the polymer material to extend around the first projections and second projections and against surfaces of the plate, the outsole, and the mold to form a fluid-filled chamber, the first projections and second projections forming bonded areas of the chamber.

17. The method recited in claim 16, wherein the step of locating includes selecting the polymer material to be a parison.

18. The method recited in claim 16, wherein the step of shaping includes bonding the polymer material to each of the plate and the outsole.

19. The method recited in claim 16, wherein the step of shaping includes sealing air at a substantially ambient pressure within the chamber.

20. A method of manufacturing an article of footwear having a sole structure, the method comprising steps of:
    providing a mold with a first mold portion and a second mold portion that cooperatively define a cavity with a shape of the sole structure;
    inserting a first sole element into a portion of the cavity formed by the first mold portion;
    inserting a second sole element into a portion of the cavity formed by the second mold portion, the second sole element having a configuration of an outsole;
    locating a polymer material between the first mold portion and the second mold portion; and
    shaping the polymer material against surfaces of the first sole element, the second sole element, and the cavity to form a fluid-filled chamber from the polymer material and to bond the first sole element and the second sole element to the chamber; and
    incorporating the first sole element, the chamber, and the second sole element into the article of footwear, the chamber forming at least a portion of a side surface of the article of footwear.

* * * * *